US005807989A

United States Patent [19]
Margolis et al.

[11] Patent Number: 5,807,989
[45] Date of Patent: Sep. 15, 1998

[54] METHODS FOR TREATMENT OR DIAGNOSIS OF DISEASES OR DISORDERS ASSOCIATED WITH AN APB DOMAIN

[75] Inventors: Benjamin Lewis Margolis; Joseph Schlessinger; Vijay Yajnik, all of New York, N.Y.

[73] Assignee: New York University, New York, N.Y.

[21] Appl. No.: 363,215

[22] Filed: Dec. 23, 1994

[51] Int. Cl.$^6$ .............................. C07K 4/12; C07K 5/00
[52] U.S. Cl. ............................................. 530/350; 436/64
[58] Field of Search ............................................. 530/350

[56] References Cited

U.S. PATENT DOCUMENTS

| | | |
|---|---|---|
| 3,691,016 | 9/1972 | Patel . |
| 3,969,287 | 7/1976 | Jaworek et al. . |
| 4,195,128 | 3/1980 | Hildebrand et al. . |
| 4,229,537 | 10/1980 | Hodgins et al. . |
| 4,247,642 | 1/1981 | Hirohara et al. . |
| 4,376,110 | 3/1983 | David et al. . |
| 4,946,778 | 8/1990 | Ladner et al. . |

OTHER PUBLICATIONS

Aaronson, "Growth Factors and Cancer", Science 254:1146–1153 (1991).
Adelman et al., "In Vitro Deletional Mutagenesis for Bacterial Production of the 20,000–Dalton Form of Human Pituitary Growth Hormone", DNA 2:183–193 (1983).
Barbacid et al, "The trk family of tyrosine kinase receptors", Biochimica et Biophysica Acta 1072:115–127 (1991).
Bargmann et al., "The neu oncogene encodes an epidermal growth factor receptor–related protein", Nature 319:226–230 (1986).
Bird et al., "Single–Chain Antigen–Binding Proteins", Science 242:423–426 (1988).
Blaikie et al., "A Region in Shc Distinct from the SH2 Domain Can Bind Tyrosine–phosphorylated Growth Factor Receptors," J. Biol. Chem. 269:32031–32034 (1994).
Bongarzone et al., "High frequency of activation of tyrosine kinase oncogenes in human papillary thyroid carcinoma", Oncogene 4:1457–1462 (1989).
Campbell et al., "Poloyma middle tumor antigen interacts with SHC protein via the NPTY (Asn–Pro–Thr–Tyr) motif in middle tumor antigen," Proc. Natl. Acad. Sci. USA 91:6344–6348 (1994).
Colbère–Garapin et al., "A New Dominant Hybrid Selective Marker for Higher Eukaryotic Cells", J. Mol. Biol. 150:1–14 (1981).
Cole et al., "The EBV–Hybridoma Technique and its Application to Human Lung Cancer", pp. 77–96 in Monoclonal Antibodies and Cancer Therapy, eds. Reisfeld and Sell, Alan R. Liss, Inc., New York (1985).
Coussens et al., "Tyrosine Kinase Receptor with Extensive Homology to EGF Receptor Shares Chromosomal Location with neu Oncogene", Science 230:1132–1139 (1985).
Creighton, Proteins: Structures and Molecular Principles, pp. 79–86, W.H. Freeman and Co., New York, (1983).
Davies, "Tracking neurotrophin function", Nature 368:193–194 (1994).
Dougall et al., "The neu–oncogene: signal transduction pathways, transformation mechanisms and evolving therapies," Oncogene 9:2109–2123 (1994).
Fingl and Woodbury, Chapter 1, pp.1–46 in The Pharmacological Basis of Therapeutics (5th edition), eds. Goodman et al., MacMillan Publishing Co., Inc., New York (1975).
Fry et al., "New insights into protein–tyrosine kinase receptor signaling complexes," Protein Science 2:1785–1797 (1993).
Hardie, D.G., "Roles of Protein Kinases and Phosphatases in Signal Transduction", Symp. Soc. Exp. Bio. 44:241–255 (1990).
Harris et al., "Breast Cancer (First of Three Parts)", New England J. of Medicine 327:319–328 (1992).
Hunter, T., "Cooperation between Oncogenes", Cell 64:249–270 (1991).
Huse et al., "Generation of a Large Combinatorial Library of the Immunoglobulin Repertoire in Phage Lambda", Science 246:1275–1281 (1989).
Huston et al., "Protein engineering of antibody binding sites: Recovery of specific activity in an anti–digoxin single–chain Fv analogue produced in Escherichia coli", Proc. Natl. Acad. Sci. USA 85:5879–5883 (1988).
Inouye and Inouye, "Up–promotor mutations in the lpp gene of Escherichia coli", Nucleic Acids Research 13:3100–3111 (1985).
Kaplan et al., "The trk Proto–Oncogene Product: A Signal Transducing Receptor for Nerve Growth Factor", Science 252:554–558 (1991).
Kavanaugh and Williams, "An Alternative to SH2 Domains for Binding Tyrosine–Phosphorylated Proteins," Science 266:1862–1866 (1994).
Klein et al., "The trkB Tyrosine Protein Kinase is a Receptor for Brain–Derived Neurotrophic Factor and Neurotrophin–3", Cell 66:395–403 (1991).
Klein et al., "Disruption of the neurotrophin–3 receptor gene trkC eliminates la muscle afferents and results in abnormal movements", Nature 368:249–251 (1994).
Koch et al., "SH2 and SH3 Domains: Elements That Control Interactions of Cytoplasmic Signaling Proteins", Science 252:668–674 (1991).
Köhler and Milstein, "Continuous cultures of fused cells secreting antibody of predefined specificity", Nature 256:495–497 (1975).

(List continued on next page.)

Primary Examiner—Toni R. Scheiner
Attorney, Agent, or Firm—Lyon & Lyon LLP

[57] ABSTRACT

The present invention concerns methods for diagnosis and treatment of diseases or disorders characterized by abnormal cellular signal transduction involving a newly identified region, herein termed the "APB domain." APB domain binding between proteins is believed to play an important role in signal transduction pathways and, thereby, influence cellular events. Thus, APB mediated activity plays a role in signal transduction pathways and agents modulating APB mediated activity can be used to treat diseases or disorders involving proteins containing APB domains.

8 Claims, 4 Drawing Sheets

OTHER PUBLICATIONS

Lam et al., "A new type of synthetic peptide library for identifying ligand–binding activity", *Nature* 354:82–84 (1991).

Logan and Shenk, "Adenovirus tripartite leader sequence enhances translation of mRNAs late after infection", *Proc. Natl. Acad. Sci. USA* 81:3655–3659 (1984).

Lowy et al., "Isolation of Transforming DNA: Cloning the Hamster aprt Gene", *Cell* 22:817–823 (1980).

Marasco et al., "Design, intracellular expression, and activity of a human anti–human immunodeficiency virus type 1 gp120 single–chain antibody", *Proc. Natl. Acad. Sci. USA* 90:7889–7893 (1993).

Marshall, "Search for a Killer: Focus Shifts form Fat to Hormones", *Science* 259:618–621 (1993).

Martin–Zanca et al., "A human oncogene formed by the fusion of truncated tropomyosins and protein tyrosine kinase sequences", *Nature* 319:743–748 (1986).

Mayer et al., "A novel viral oncogene with structural similarity to phospholipase C", *Nature* 332:272–275 (1988).

Miller, "Human gene therapy comes of age", *Nature* 357:455–460 (1992).

Morrison et al., "Chimeric human antibody molecules: Mouse antigen–binding domains with human constant region domains", *Proc. Natl. Acad. Sci. USA* 81:6851–6855 (1984).

Mulligan and Berg, "Selection for animal cells that express the *Escherichia coli* gene coding for xanthine–guanine phosphoribosyltransferase", *PNAS* 78:2072–2076 (1981).

Musacchio et al., "The PH domain: a common piece in the structural patchwork of signalling proteins", *TIBS* 18:343–348 (1993).

Neuberger et al., "Recombinant antibodies possessing novel effector functions", *Nature* 312:604–608 (1984).

O'Hare et al., "Transformation of mouse fibroblasts to methotrexate resistance by a recombinant plasmid expressing a prokaryotic dihydrfolate reductase", *PNAS* 78:1527–1531 (1981).

Obermeier et al., "Tyrosine 785 is a major determinate of Trk–substrate interaction", *The EMBO Journal* 12:933–941 (1993).

Obermeier et al., "Identification of Trk Binding Sites for SHC and Phosphatidylinositol 3'–Kinase and Formation of a Multimeric Signaling Complex", *J. Bio. Chem.* 268:22963–22966 (1993).

Padhy et al., "Identification of a Phosphoprotein Specifically Induced by the Transforming DNA of Rat Neuroblastomas", *Cell* 28:865–871 (1982).

Park et al., "Mechanism of met Oncogene Activation", *Cell* 45:895–904 (1986).

Pawson and Gish, "SH2 and SH3 Domains: From Structure to Function", *Cell* 71:359–362 (1992).

Pawson and Schlessinger, "SH2 and SH3 domains", *Current Biology* 3(7):434–442 (1993).

Pendergast et al., "BCR–ABL–Induced Oncogenesis is Mediated by Direct Interaction with the SH2 Domain of the GRB–2 Adaptor Protein," *Cell,* 75:175–185 (1993).

Plowman et al., "Heregulin induces tyrosine phosphorylation of HER4/p180$^{erbB4}$", *Nature* 366:473–475 (1993).

Posada and Cooper, "Molecular Signal Integration. Interplay Between Serine, Threonine and Tyrosine Phosphorylation", *Mol. Biol. of the Cell* 3:583–592 (1992).

Pulciani et al., "Oncogenes in solid human tumours", *Nature* 300:539–542 (1982).

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$, *Mol. and Cell. Biol.* 6:4396–4408 (1986).

Santerre et al., "Expression of prokaryotic genes for hygromycin B and G418 and G418 resistance as dominant–selection markers in mouse L Cells", *Gene* 30:147–156 (1984).

Schechter et al., "The neu oncogene: an erb–B–related gened encoding a 185,000–M$_r$ tumour antigen", *Nature* 312:513–516 (1984).

Schlessinger and Ullrich, "Growth Factor Signaling by Receptor Tyrosine Kinases", *Neuron* 9:383–391 (1992).

Samanta et al., "Ligand and p185$^{c-neu}$ density govern interactions and tyrosine kinase activation," *Proc. Natl. Acad. Sci. USA* 91:1711–1715 (1994).

Schlessinger, "Signal transduction by allosteric receptor oligomerization", *Trends Biochem. Sci.* 13:443–447 (1988).

Slamon et al., "Human Breast Cancer: Correlation of Relapse and Survival with Amplification of the HEr–2/neu Oncogene", *Science* 235:177–185 (1987).

Slamon et al., "Studies of the HER–2/neu Proto–oncogene in Human Breast and Ovarian Cancer", *Science* 244:707–712 (1989).

Sliwkowski et al., "Coexpression of erbB2 and erbB3 Proteins Reconstitutes a High Affinity Receptor for Heregulin", *J. Biol. Chem.* 269:14661–14665 (1994).

Smeyne et al., "Severe sensory and sympathetic neuropathies in mice carrying a disrupted Trk/NGF receptor gene", *Nature* 368:246–248 (1994).

Songyang et al., "SH2 Domains Recognize Specific Phosphopeptide Sequences", *Cell* 72:767–778 (1993).

Szybalska and Szybalski, "Genetics of Human Cell Lines, IV. DNA–Mediated Heritable Transformation of a Biochemical Trait", *PNAS* 48:2026–2034 (1962).

Takeda et al., "Construction of chimaeric processed immunoglobulin genes containing mouse variable and human constant region sequences", *Nature* 314:452–454 (1985).

Ullrich and Schlessinger, "Signal Transduction by Receptors with Tyrosine Kinase Activity", *Cell* 61:203–212 (1990).

Van Heeke and Schuster, "Expression of Human Asparagine Synthetase in *Escherichia coli*", *J. Biol. Chem.* 264:5503–5509 (1989).

Wada et al., "Intermolecular Association of the p185$^{neu}$ Protein and EGF Receptor Modulates EGF Receptor Function," *Cell* 61:1339–1347 (1990).

Ward et al., "Binding activities of a repertoire of single immunoglobulin variable domains secreted from *Escherichia coli*", *Nature* 341:544–546 (1989).

Wigler et al., "Transfer of Purified Herpes Virus Thymidine Kinase Gene to Cultured Mouse Cells", *Cell* 11:223–232 (1977).

Wigler et al., "Transformation of mammalian cells with an amplifiable dominant–acting gene", *PNAS* 77:3567–3570 (1980).

Yamamoto et al., "Similarity of protein encoded by the human C–erb–B–2 gene to epidermal growth factor receptor", *Nature* 319:230–234 (1986).

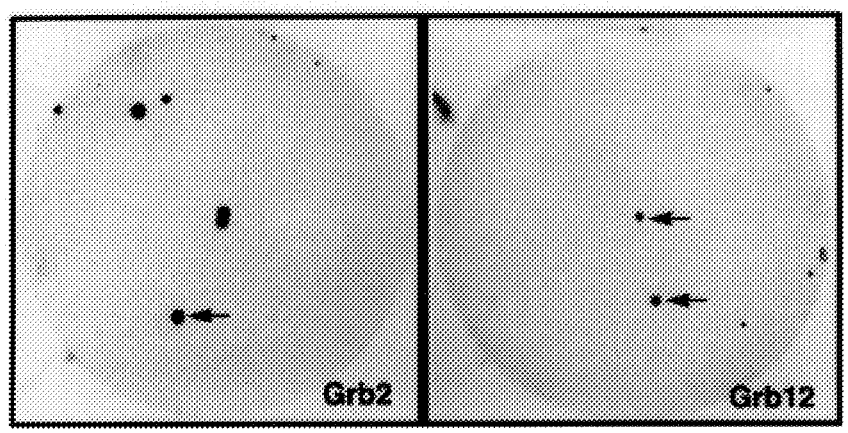

```
Murine    1   MNKLSGGGGRRTRVEGGQLGGEEWTRHGSFVNKPTRGWLHPNDKVMGPGVSYLVRYMGCV
Human     1   ............................................................

Murine   61   EVLQSMRALDFNTRTQVTREAISLVCEAVPGAKGATRRRKPCSRPLSSILGRSNLKFAGM
Human    61   ............................................................

Murine  121   PITLTVSTSSLNLMAADCKQIIANHRMQSISFASGGDPDTAEYVAYVAKDPVNQRACHIL
Human   121   ............................................................

Murine  181   ECPEGLAQDVISTIGQAPELRFKQYLRNPPKLVTPHDRMAGFDGSAWDEEEEEPPDHQYY
Human   181   ............................................................

Murine  241   NDFPGKEPPLGGVVDMRLRE----GAARPTLPSAQMSSHLGATLPIGQHAAGDHEVRKQM
Human   241   ....................GAAP......A.N..TP........V..PVG..P......

Murine  297   LPPPPCPGRELFDDPSYVNIQNLDKARQAGGGAGPPNPSLNGSAPRDLFDMKPFEDALRV
Human   301   P...............V.........V.......AI....................

Murine  357   PPPPQSMSMAEQLQGEPWFHGKLSRRREAEALLQLNGDFLVRESTTTPGQYVLTGLQSGQP
Human   361   ......V......R..............................................

Murine  417   KHLLLVDPEGVVRTKDHRPESVSHLISYHMDNHLPIISAGSELCLQQPVDRKV
Human   421   ..................................................E..L
```

FIG. 1.

METHODS FOR TREATMENT OR DIAGNOSIS OF DISEASES OR DISORDERS ASSOCIATED WITH AN APB DOMAIN

FIELD OF THE INVENTION

The present invention relates generally to the fields of chemistry, biology, and medicine and more specifically to the diagnosis and treatment of various diseases or disorders.

BACKGROUND OF THE INVENTION

The following is a discussion of relevant art none of which is admitted to be prior art to the invention.

Receptor tyrosine kinases belong to a family of transmembrane proteins and have been implicated in cellular signaling pathways. The predominant biological activity of some receptor tyrosine kinases is the stimulation of cell growth and proliferation, while other receptor tyrosine kinases are involved in arresting growth and promoting differentiation. In some instances, a single tyrosine kinase can inhibit, or stimulate, cell proliferation depending on the cellular environment in which it is expressed. (Schlessinger, J. and Ullrich, A., Neuron, 9(3):383–391, 1992.)

Receptor tyrosine kinases are composed of at least three domains: an extracellular ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues. Individual phosphotyrosine residues of the cytoplasmic domains of receptors may serve as specific binding sites that interact with a host of cytoplasmic signalling molecules, thereby activating various signal transduction pathways (Ullrich, A. and Schlessinger, J., 1990, Cell 61:203–212).

The intracellular, cytoplasmic, non-receptor protein tyrosine kinases do not contain a hydrophobic transmembrane domain and share non-catalytic domains in addition to sharing their catalytic kinase domains. Such non-catalytic domains include the SH2 domains (SRC homology domain 2; Sadowski, I. et al., Mol. Cell. Biol. 6:4396–4408; Koch, C. A. et al., 1991, Science 252:668–674) and SH3 domains (SRC homology domain 3; Mayer, B. J. et al., 1988, Nature 332:269–272). Such non-catalytic domains are also thought to include the PH domain (Musacchio et al., 1993, TIBS 18:342–348). The non-catalytic domains are thought to be important in the regulation of protein-protein interactions during signal transduction (Pawson, T. and Gish, G., 1992, Cell 71:359–362).

A central feature of signal transduction (for reviews, see Posada, J. and Cooper, J. A., 1992, Mol. Biol. Cell 3:583–392; Hardie, D. G., 1990, Symp. Soc. Exp. Biol. 44:241–255), is the reversible phosphorylation of certain proteins. Receptor phosphorylation stimulates a physical association of the activated receptor with target molecules. Some of the target molecules are in turn phosphorylated. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras Pawson, T. and Schlessinger, J., Current Biol. 13:434, 1993.

The secondary signal transducer molecules generated by activated receptors result in a signal cascade that regulates cell functions such as cell division or differentiation. Reviews describing intracellular signal transduction include Aaronson, S. A., Science, 254:1146–1153, 1991; Schlessinger, J. Trends Biochem. Sci., 13:443–447, 1988; and Ullrich, A., and Schlessinger, J., Cell, 61:203–212, 1990.

Abnormalities in signal transduction pathways can lead to various diseases in at least three different ways: (1) under-activity (2) mutation, and (3) over-activity. An example of under-activity is observed in some forms of diabetes. Examples of mutation include the role of BCRABL in chronic myelogenous leukemia and acute lymphocytic leukemia. Pendergrast et al., 1993, Cell 75:175–185.

Over-activity of certain protein tyrosine kinases has been shown to subvert normal growth control pathways and lead to oncogenesis (reviewed in Hunter, T., 1991, Cell 64:249–270). An example of a protein that may participate in the aberrant growth of breast cancer cells is HER2, also known as c-erbB-2 (Coussens et al., 1985 Science 230:1132–1139; Yamamoto et al., 1986, Nature, 319:521–527). This receptor was also isolated as the rat oncogene neu, an oncogene responsible for chemically induced rat glioblastomas (Padhy et al., 1982 Cell, 28:865–871; Schechter et al., 1984 Nature 312:513–516; Bargmann et al., 1986, Nature, 319:226–230). HER2/erbB-2 is known to be amplified and over-expressed in about 25% of human breast cancers (Slamon et al., 1987 Science 235:177–182; Slamon et al., 1989 Science 244:707–712).

SUMMARY OF THE INVENTION

The present invention concerns methods for diagnosis and treatment of diseases or disorders characterized by abnormal cellular signal transduction involving a newly identified region, herein termed the "APB domain." APB domain binding between proteins is believed to play an important role in signal transduction pathways and, thereby, influence cellular events. Thus, APB mediated activity plays a role in signal transduction pathways and agents modulating APB mediated activity can be used to treat diseases or disorders involving proteins containing APB domains.

For example, phosphorylated receptor tyrosine kinases such as EGF, TrkA, and HER-2 have an APB recognition region able to bind to an APB domain present in an adapter molecule such as Shc. The bound adapter molecule is in turn phosphorylated and can interact with other molecules. Thus, signal transduction starting with phosphorylation of a receptor tyrosine kinase is in part transmitted through APB binding and modulating APB mediated activity will increase or decrease such signal transduction.

An example of an APB domain is that present in the N-terminal amino acids 1–163 of 46 Kd Shc (p46$^{shc}$), and amino acids 46–209 of 52 Kd Shc (p52$^{shc}$) (see Example infra). Other proteins having an APB domain are believed to exist or can be produced synthetically. Such other APB domains have at least 20% sequence identity or at least 30% sequence similarity with the APB domain present in Shc (i.e., amino acid 46–209 of p52$^{shc}$).

The APB domain can bind to a protein amino acid region (i.e. an "APB recognition" region) present in a protein binding partner. A broad range of sequences may be capable of interacting with an APB domain. The APB domain is believed to bind to a recognition region of at least 10 amino acids containing the amino acid sequence asparagine-proline-X-(phosphorylated)tyrosine, where X refers to any amino acid. Numerous proteins having APB recognition domains are known in the art, see for example Campbell et al., *Proc. Natl. Acad. Sci. USA* 91:6344, 1994, hereby incorporated by reference herein. Kavanaugh and Williams *Science* 266:1862, 1994 (not admitted to be prior art), identify a protein domain present in Shc that specifically binds to the tyrosine-phosphorylated form of its target at a domain other than SH2 sequences.

The present invention provides a target site for designing therapeutic and diagnostic agents. The present disclosure allows for the design of therapeutic agents able to modulate APB mediated activity between proteins and, thus alter signal transduction. Preferred modulating agents can decrease signal transduction from a receptor tyrosine kinase by disrupting binding involving an APB domain.

Thus, a first aspect of the present invention features a method for treating a disease or disorder in an organism characterized by an abnormal level of interaction between an APB domain and its binding partner. The disease or disorder may also be characterized by an abnormality in a signal transduction pathway, wherein the pathway contains a protein with an APB domain. The method includes disrupting or promoting that interaction (or signal) in vivo. The method also involves inhibiting the activity of the complex formed between the APB domain-containing protein and its binding partner.

By "organism" is meant any living creature. The term includes mammals, and specifically humans.

An "abnormal level" of interaction refers to a different level of interaction than occurring in the general population of healthy organisms. The abnormal level can be an increased amount or a decreased amount. The abnormality in signal transduction may be realized as an abnormality in cell growth, migration or other function.

By "signal transduction pathway" is meant the sequence of events that involves the transmission of a message from an extracellular protein to the cytoplasm through a cell membrane. The signal ultimately will cause the cell to perform a particular function, for example, to proliferate and therefore cause cancer. Various mechanisms for the signal transduction pathway (Fry et al., 1993, Protein Science, 2:1785–1797) provide possible methods for measuring the amount or intensity of a given signal.

Depending upon the particular disease associated with the abnormality in a signal transduction pathway, various symptoms may be detected. For example, if the disease is breast cancer, one may detect cell proliferation or tumor size, among other symptoms.

Furthermore, since some adaptor molecules recruit secondary signal transducer proteins towards the membrane, one measure of signal transduction is the concentration and localization of various proteins and complexes. In addition, conformational changes involved in the transmission of a signal may be observed using circular dichroism and fluorescence studies.

Another aspect of the present invention describes a method for treating a patient having a disease or disorder characterized by APB binding involving the step of administering to the patient a therapeutically effective amount of an agent which decreases binding between an APB recognition region present in a first protein and an APB domain present in a second protein. A "patient" refers to human, who preferably has a cell proliferative disorder involving a receptor tyrosine kinase.

Preferably, the first protein is a receptor tyrosine kinase, the second protein is Shc, and the agent decreases one or more activities of the receptor tyrosine kinase by decreasing signal transduction from Shc. More preferably, the receptor tyrosine kinase is either EGF, HER-2, or TrkA.

The agent decreases APB mediated activity. The effect on APB mediated activity can be determined using standard techniques which depend on the type of activity being mediated. For example, different activities of EGF, HER-2, or TrkA can be measured downstream of Shc binding.

A "therapeutic effective amount" generally refers to an amount which inhibits, to some extent, growth of cells causing or contributing to a cell proliferative disorder and brings about a therapeutic effect in a human. "Cell proliferative disorders" refer to disorders wherein unwanted cell proliferation of one or more subset(s) of cells in a multicellular organism occurs, resulting in harm (e.g., discomfort or decreased life expectancy) to the multicellular organism. Cell proliferative disorders can occur in different types of animals and in humans. Cell proliferative disorders include cancers, blood vessel proliferative disorders, and fibrotic disorders.

A therapeutic effect relieves to some extent one or more of the symptoms of a cell proliferative disease or disorder. In reference to the treatment of a cancer, a therapeutic effect refers to one or more or the following: 1) reduction in tumor size; 2) inhibition (i.e., slowing to some extent, preferably stopping) of tumor metastasis; 3) inhibition, to some extent, of tumor growth; and 4) relieving to some extent one or more of the symptoms associated with the disease or disorder.

In reference to treating a cell proliferative disease or disorder other than a cancer, a therapeutic effect refers to one or more of the following: 1) the inhibition, to some extent, of the growth of cells causing the disease or disorder; 2) the inhibition, to some extent, of the production of factors (e.g., growth factors) causing the disorder; and 3) relieving to some extent one more or the symptoms associated with the disease or disorder. The disease or disorder may be characterized by an abnormality in the signal transduction pathway even if the level of interaction between the APB domain and its binding partner is normal.

"Characterized by APB binding" refers to the involvement of APB binding in causing or accentuating to some extent, the disease or disorder. For example, APB binding of Shc can lead to phosphorylation of Shc which in turn can interact with Ras leading to transformation of a cell thereby causing cancerous growth. Shc activation may also aid in the transformation of cells by other mechanisms and may exert other harmful effects.

Agents able to modulate APB mediated activity are generally targeted to modulate APB mediated activity in one or more of the following ways: (1) by binding to the APB domain thereby inhibiting subsequent protein binding; (2) by binding to an APB recognition region thereby inhibiting subsequent protein binding; (3) by binding to the APB domain and producing either an increase or decrease in signal transduction; and (4) by binding to an APB recognition region and producing either an increase or decrease in signal transduction. Examples of such agents include organic molecules, preferably 150 to 1,000 daltons, and polypeptides or antibodies able to bind to the APB domain or APB recognition region.

Another aspect of the present invention features a method for screening for an agent useful for treatment of disease or disorder characterized by abnormal APB binding. The method involves assaying potential agents for the ability to disrupt or promote that interaction. The screening may also involve assaying potential agents for the ability to remove or reduce an abnormality in a signal transduction pathway, wherein the signal transduction pathway contains a protein with an APB domain.

Another aspect of the present invention describes a method for diagnosing a disease or disorder characterized by an abnormal level of APB mediated activity. The method includes the step of detecting the level of APB binding between an APB recognition region present in a first protein and an APB domain present in a second protein.

Assays to detect the level of APB binding can be carried out using different techniques. For example, cells can be isolated from a patient and the level of interaction can be measured using a competitive or non-competitive assay formats involving an APB recognition binding agent or an APB domain binding agent.

Another aspect of the present invention describes a method of assaying for agents useful for disrupting APB interactions or in the diagnosis of APB diseases or disorders. The method involves the step of measuring the ability of an agent to bind to an APB recognition region or an APB domain.

Another aspect of the present invention describes a purified recombinant polypeptide encoding a APB domain having at least 20% sequence identity or 30% sequence similarity to the APB domain present in Shc. By "recombinant" is meant that the APB domain is present on a polypeptide fragment. The polypeptide fragment is obtained from a particular source such as Shc or synthetically produced, contains an APB region having at least 20% sequence identity or 30% sequence similarity to the Shc APB region, and is less than the full length Shc. Thus, the present invention also features a peptide comprising, consisting or consisting essentially of an APB domain.

By "purified" is meant that the polypeptide is in a form (i.e., its association with other molecules) distinct from naturally occurring polypeptide. Preferably, the polypeptide is provided as a substantially purified preparation representing at least 75%, more preferably at least 85%, most preferably at least 95% of the total protein in the preparation.

Other features and advantages of the invention will be apparent from the following description of the preferred embodiments thereof, and from the claims.

BRIEF DESCRIPTION OF THE DRAWINGS

FIG. 1. Cloning of murine p52$^{Shc}$. A, binding of EGF receptor probe to Grb2 or Grb12 expressing λEXlox phages. Arrows indicate examples of positive plaques. B, amino acid sequence alignment of human and murine p52$^{Shc}$. Dots indicate identical residues; dashed line indicates a gap in the murine sequence.

FIG. 2A, HER14 lysates from either EGF-stimulated (+) or unstimulated (−) cells (5×10$^6$ cells) were incubated with 3 μg of GST fusion protein immobilized on glutathione-agarose beads. The bound proteins were washed, subjected to SDS-PAGE, transferred to nitrocellulose and immunoblotted with anti-EGF receptor antibody, anti-C (anti-EGFR). HER14 lysate (4×10$^5$ cells) was run directly on the gel in lanes 5 and 6. FIG. 2B, unstimulated HER14 lysates (5×10$^6$ cells) were immunoprecipitated with anti-EGFR antibody (mAb 108). The immobilized receptor was then phosphorylated (+) by the addition of 5 mM MnCl$_2$ and 50 μM ATP or left unphosphorylated (−) by adding MnCl$_2$ alone. Bacterial lysates containing 5 μg of GST, GST-Grb7, and GST-Shc 1-209 were then diluted in 1 ml of 1% Triton X-100 lysis buffer, added to the immobilized receptor and incubated at 4° C. for 90 min. The bound proteins were washed and together with 40 μl of the post-binding supernatant separated by SDS-PAGE and transferred to nitrocellulose. The bound fractions (left panel) and supernatants (right panel) were immunoblotted with anti-GST.

FIG. 4A, schematic diagram illustrating the Shc fragments used in binding studies. Full length murine p52$^{Shc}$ is indicated in (i) while (ii)–(vi) were generated as GST fusion proteins for use in receptor binding studies. FIG. 4B, association of various GST fusion proteins with activated EGF receptor (EGFR). Binding was performed as in FIG. 2A with the exception that all lysates were stimulated with EGF. All studies used 3 μg of fusion proteins except for the Shc SH2 where 10 μg was used. Immunoblotting was performed with anti-phosphotyrosine. FIG 4C, binding of Shc fusion proteins to NIH 3T3 cells expressing a HER1/2 chimera. This chimera consists of the EGF receptor extracellular binding domain and the intracellular region of HER2/neu. After stimulation of these cells with EGF (200 ng/ml) lysates were prepared and binding as well as blotting studies were performed as in B using anti-phosphotyrosine antibody. FIG. 4D, binding of Shc 1-209 to TrkA. Beads containing 10 μg of GST fusion proteins Shc 1-209, phospholipase C-γ (PLC-γ) SH2 (contains both N and C SH2 domains), or GST alone were added to lysates from 2×10$^7$ PC12 cells stimulated with 50 ng/ml nerve growth factor (lanes 1, 2, and 4). The binding of the same amount of lysate to 2 μg of anti-TrkA antibody is shown as a positive control and to indicate the position of TrkA on the blot (lane 3). Otherwise, the binding and blotting were performed as in B using anti-phosphotyrosine antibody.

DESCRIPTION OF THE PREFERRED EMBODIMENTS

Figure 2A:
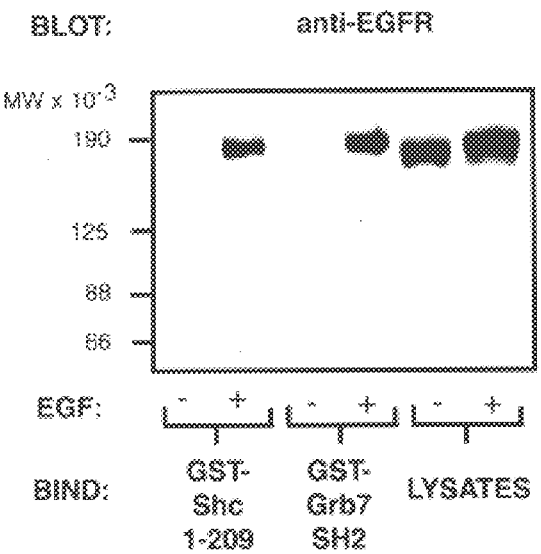
FIGS. 2A and 2B. Association of GST-Shc 1-209 with the EGF Receptor (EGFR).

The present invention identifies the APB domain as a target site for diagnostic agents, and therapeutic agents able to modulate one or more APB mediated activities. Different diseases or disorders involving APB domain binding between proteins can be targeted by the present invention. The therapeutic agents can modulate signal transduction and, thereby, can be used to treat diseases or disorders where signal transduction plays a role. For example, the interaction of the APB domain of Shc with EGF, TrkA, and HER-2 is described below. By disrupting such interaction diseases associated with EGF, TrkA, or HER-2 activation can be treated.

I. TARGETED DISEASES

The identification of the APB domain and its ability to play a role in signal transduction allows for targeting a wide range of diseases or disorders associated with tyrosine kinase activity. Examples of proteins binding the APB domain include EGF, HER-2 and TrkA. These proteins are receptor tyrosine kinases which have different diseases or disorders associated with their activation and subsequent signal transduction. By modulating APB domain binding to such receptor tyrosine kinases the associated disease can be treated. Examples of diseases associated with EGF, HER-2 and TrkA are described in sections IA–IC infra.

Additionally, a disorder involving a protein-protein complex may, for example, develop because the presence of such a complex brings about the aberrant inhibition of a normal signal transduction event. In such a case, the disruption of the complex would allow the restoration of the usual signal transduction event. Further, an aberrant complex may bring about an altered subcellular adaptor protein localization, which may result in, for example, dysfunctional cellular events. An inhibition of the complex in this case would allow for restoration or maintenance of a normal cellular architecture. Still further, an agent or agents that cause(s) disruption of the complex may bring about the disruption of the interactions among other potential components of a complex.

Additional diseases or disorders which can be targeted by the present invention can be identified using the present disclosure as guide. Both APB domain containing proteins and APB recognition region proteins can be identified. For example, the identification of Shc as containing an APB domain is described in the Example below. Additional proteins containing an APB domain can be obtained by repeating the procedure or by equivalent methods. Proteins containing an APB recognition domain can be identified using a similar procedure starting with a labeled APB domain binding protein. For example, a labeled Shc protein.

A. EGFR Cell Proliferation Disorders

EGFR cell proliferation disorders are characterized by inappropriate EGFR activity. "Inappropriate EGFR" activity refers to either 1) EGF-receptor (EGFR) expression in cells which normally do not express EGFR; 2) EGF expression by cells which normally do not express EGF; 3) increased EGF-receptor (EGFR) expression leading to unwanted cell proliferation; 4) increased EGF expression leading to unwanted cell proliferation; and/or 5) mutations leading to constitutive activation of EGF-receptor (EGFR). The existence of inappropriate or abnormal EGF and EGFR levels or activities can be determined by procedures well known in the art.

An increase in EGF activity or expression is characterized by an increase in one or more of the activities which can occur upon EGF ligand binding such as: (1) auto-phosphorylation of EGFR, (2) phosphorylation of an EGFR substrate (e.g., PLC$\gamma$, see Fry supra), (3) activation of an adapter molecule, and/or (4) increased cell division. These activities can be measured using techniques known in the art. For example auto-phosphorylation of EGFR can be measured using an anti-phosphotyrosine antibody, and increased cell division can be performed by measuring $^3$H-thymidine incorporation into DNA.

Unwanted cell proliferation can result from inappropriate EGFR activity occurring in different types of cells including cancer cells, cells surrounding a cancer cell, and endothelial cells. Examples of disorders characterized by inappropriate EGF activity include cancers such as glioma, head, neck, gastric, lung, breast, ovarian, colon, and prostate; and other types of cell proliferative disorders such as psoriasis.

B. HER2 Cell Proliferation Disorders

HER2 cell proliferation disorders are characterized by over-activity of HER2. Over-activity of HER2 refers to either an amplification of the gene encoding HER2 or the production of a level of HER2 activity correlated with a cell proliferative disorder (i.e., as the level of HER2 increases the severity of one or more of the symptoms of the cell proliferative disorder increases).

Activation of HER-2 protein can be caused by different events such as ligand-stimulated homo-dimerization, ligand-stimulated hetero-dimerization and ligand-independent homo-dimerization. Ligand-stimulated hetero-dimerization appears to be induced by EGFR to form EGF-R/HER-2 complexes and by neu differentiation factor/heregulin (NDF/HRG) to form HER-2/HER-3 and/or HER-2/HER-4 complexes. Wada et al., *Cell* 61:1339, 1990; Slikowski et al., *J. Biol. Chem.* 269:14661, 1994; Plowman et al., *Nature* 266:473, 1993. Ligand-dependent activation of HER2 protein is thought to be mediated by neu-activating factor (NAF) which can directly bind to p185(HER-2) and stimulate enzymatic activity. Dougall et al., *Oncogene* 9:2109, 1994; Samata et al., *Proc. Natl. Acad. Sci. USA* 91:1711, 1994. Ligand-independent homo-dimerization of HER2 protein and resulting receptor activation is facilitated by over-expression of HER2 protein.

HER2 activity can be assayed by measuring one or more of the following activities: (1) phosphorylation of HER2; (2) phosphorylation of a HER2 substrate; (3) activation of an HER2 adapter molecule; and (4) increased cell division. These activities can be measured using techniques described known in the art.

Patients suffering from a HER2 driven disease or disorder can be identified by analysis of their symptoms by procedures well known to medical doctors. Such identified patients can then be treated as described herein.

HER2 driven diseases or disorders are typically cell proliferative disorders such as cancers. HER2 driven disorders appear to be responsible for a sub-population of different types of cancers. For example, Slamon et al., *Science* 244:707, 1989, examined the correlation between HER-2/neu and breast and ovarian carcinoma, and also examined procedures used to measure the correlation. According to Slamon:

The HER-2/neu proto-oncogene is amplified in 25 to 30 percent of human primary breast cancers and this alteration is associated with disease behavior. In this report, several similarities were found in the biology of HER-2/neu in breast and ovarian cancer, including a similar incidence of amplification, a direct correlation between amplification and over-expression, evidence of tumors in which overexpression occurs without amplification, and the association between gene alteration and clinical outcome. A comprehensive study of the gene and its products (RNA and protein) was simultaneously preformed on a large number of both tumor types. This analysis identified several potential shortcomings of the various methods used to evaluate HER-2/neu in these diseases (Southern, Northern, and Western blots, and immunohistochemistry) and provided information regarding considerations that should be addressed when studying a gene or gene product in human tissue. The data presented further support the concept that the HER-2/neu gene may be involved in the pathogenesis of some human cancers.

The use of the present invention to treat breast cancer is preferred because of the prevalence and severity of breast cancer. Carcinoma of the breast is the most common cancer among women and their second leading cause of cancer death (Marshall, E., *Science* 259:618–621, 1993). The incidence of breast cancer has been increasing over the past several decades (Marshall, supra, and Harris, J. R., et al, *New Engl. J. Med.,* 327(5):319–328, 1992). In addition to breast cancers, increased HER2 activity or gene expression has been associated with certain types of stomach adenocarcinomas, salivary gland adenocarcinomas, endometrial cancers, ovarian adenocarcinomas, gastric cancers, colorectal cancers, non-small cell lung cancer, and glioblastomas.

C. Trk Cell Proliferation Disorders

Differentiation and survival of neuronal cells is mediated, in part, by the activity of a family of related receptor tyrosine kinases, including TrkA, TrkB, and TrkC and ligands such as nerve growth factor (NGF), brain-derived neurotrophic factor (BDNF) and neurotrophins-3 and 4 (NT-3 and NT-4). Barbacid, M., *Biochimica et Biophysica Acta* 1072:115–127, 1991, Kaplan, D. R., *Science* 252:554–558, 1991; Klein, R., *Cell* 65:189–197, 1991; Davies, A. M., *Nature* 368:193–194, 1994 and Klein, R., *Cell* 66:395–403, 1991. Examples of diseases or disorders to be treated or diagnosed by targeting Trk include Alzheimer's disease, Parkinson's disease, Lou Gerhig's disease (ALS), trauma, damaged or severed nerve injuries, Huntington's chorea, multiple schleroris, muscular dystrophy, syringomiplia, Tabes Dorsalis, and cardiovascular accidents. These and other diseases or disorders are often characterized by one or more of the following symptoms: atasia, aphasia, paralysis, paresea, and paralgies.

Abnormalities in Trk signal transduction pathways can lead to various diseases through both underactivity and over-activity. Examples of disorders which are characterized by underactivity of a signal transduction pathway include various neurodegenerative diseases such as myasthenia gravis, amyotrophic lateral sclerosis, cervical spondylosis, and Alzheimer's disease. A neurological disease possibly characterized by over-activity of a signal transduction pathway is neurofibromatosis. See, in general, The Merck Manual of Diagnosis and Therapy, 16th Edition, 1992.

Mutations in the Trk gene are also involved in cancer. Mutant Trk genes have been isolated from both colon and thyroid carcinomas. In general, the mutations involve a molecular rearrangement such that the transmembrane and cytoplasmic portions of the Trk gene remain intact, however, the normal extracellular ligand binding sequences have been replaced by foreign sequences such as those coding for tropomyosin. Martin-Zanca, D., *Nature* 319:743–748, 1986, Pulciani, S., *Nature* 300:539–542, 1982, Bongarzone, I., *Oncogene* 4:1457–1462, 1989 and Park, M., *Cell* 45:895–904, 1986. Such mutations may lead to abnormal signal transduction activity by stimulating activity even in the absence of the normal ligand and/or stimulating activity in an inappropriate (non-neuronal) cell type.

The importance of the Trk gene family for the growth, differentiation and survival of nerve cells was recently demonstrated by experiments in mice. Gene targeting was used to generate mice with null mutations in genes encoding each of the known Trk receptors, and in one case the gene encoding a Trk ligand. Smeyne, R. J., et al., *Nature* 368:246–249, 1994, and Klein, R., et al., *Nature* 268:249–251, 1994. Such mice cannot express the target gene and all had severe neurological dysfunction and important types of neural tissue were absent.

The development and maintenance of cellular communication networks within the central and peripheral nervous system is regulated by neurotrophic factors, which through activation of specific cell surface receptors generate differentiation and survival signals in neuronal cell types. Binding of the neurotrophic factor to its receptor initiates a cellular signal transduction cascade involving diverse cytoplasmic components eventually resulting in a specific nuclear response. Specific cellular responses in nerve cells can include, for example, neurite outgrowth, acquisition of $Na^+$-based action potential and cell survival in serum-free medium.

The complex processes of cell growth, differentiation and cell survival are mediated by diverse and divergent signal transduction pathways. The multiple phosphorylated tyrosines found in activated receptor tyrosine kinases serve as binding sites for different signaling components, which in turn modulate the transduction of a signal along a particular pathway. In the case of the NGF receptor Trk, specific phosphorylated tyrosines within the cytoplasmic portion of the receptor can bind to the signaling components phospholipase C-gamma (PLC-gamma), Shc and the non-catalytic subunit of phosphatidylinositol-3'-kinase, p85. Obermeier, A., *EMBO Journal* 12:933–941, 1993 and Obermeier, A., *J. Biol. Chem.* 268:22963–22966, 1993.

These proteins in turn each stimulate different and distinct further downstream signaling components until instructions are finally transmitted to the cell nucleus. For example, Shc binds to the Grb2/SOS complex, which in turn allows the activation of ras.

II. THERAPEUTIC AGENTS

Different types of therapeutics agents can be used to modulate APB mediated activity such as organic molecules, inorganic molecules, and polypeptides binding to the APB domain or APB region site. Such agents can be obtained and administered using the present disclosure as a guide. For example, APB binding molecules such as organic or inorganic molecules, preferably organic molecules can be obtained as described in section III infra.

A. Polyoeptides Modulating APB Mediated Activity

Therapeutic protein or polypeptide agents can be designed to bind to an APB domain or an APB recognition region. Polypeptides binding to an APB recognition region preferably are at least 10 amino acid in length and contain the amino acid sequence asparagine-proline-X-(phosphorylated)tyrosine, where X refers to any amino acid.

The terms "protein" and "polypeptide" refers to 5 or more amino acids joined together by peptide bonds. An "amino acid" is a subunit that is polymerized to form proteins and there are twenty amino acids that are universally found in proteins. The general formula for an amino acid is $H_2N$—CHR—COOH, in which the R group can be varies from a hydrogen atom (as in the amino acid glycine) to a complex ring (as in the amino acid tryptophan).

APB amino acid recognition regions binding to an APB recognition region are preferably at least 150 amino acids in length and contain an amino acid sequence having at least 20% sequence identity or at least 30% sequence similarity to the APB domain present in Shc. In a preferred embodiment an APB domain has at least 40%, at least 65%, or at least 80% sequence identity to the APB domain present in Shc. In another preferred embodiment the APB domain has at least 50%, at least 75%, or at least 90% sequence similarity to the APB domain present in Shc.

The percentage of sequence identity between two domains is calculated by dividing the number of amino acids that are the same in a given region by the total number of amino acids in the given region. Proteins having such domains are readily identified using standard protocols. The percentage of sequence similarity can calculated using a computer program (such as the GCG Bestfit program) that scores a protein based upon the number of gaps that must be induced to achieve similarity.

Regions that have at least 20% identity or at least 30% similarity are recognized as containing the same domain independent of any knowledge of the function of the proteins or domains. However, when knowledge regarding the function of the proteins or domain is known, then equivalent domains may be identified with much lower identity or similarity. For example, the pleckstrin domain contains two proteins that only share approximately 5% identity to each other. Musacchio, supra.

B. Molecules Modulating APB mediated activity

Inorganic and organic molecules able to modulate APB mediated activity may also be used to treat diseases or disorders involving APB mediated activity. Such molecules can be obtained as described in section III infra.

C. Antibodies able to modulate APB mediated activity

Antibodies capable of binding to an APB domain or APB receptor recognition region can be used for treating diseases or disorders involving APB binding. For example, nucleotide sequences encoding single-chain antibodies targeted to an APB domain or APB receptor recognition region may be expressed within the target cell population by utilizing, for example, techniques such as those described in Marasco et al. *Proc. Natl. Acad. Sci. USA* 90:7889–7893, 1993.

Antibodies which can be used as therapeutic or diagnostic agents include polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Antibodies may be of any immunoglobulin class including IgG, IgM, IgE, IgA, IgD and any subclass thereof. Such antibodies may be used, for example, in the detection of a protein-protein complex in a biological sample, or, alternatively, as a method for the inhibition of a complex formation, thus, inhibiting the development of a disease or disorder.

Protein-protein complexes are formed between at least a protein containing an APB domain and a protein containing an APB recognition region. Under standard physiological conditions, the components of such complexes are capable of forming stable, non-covalent attachments with one or more of the other complex components.

Polyclonal antibodies are heterogeneous populations of antibody molecules derived from the sera of animals immunized with an antigen, such as a protein-protein complex, or individual components. For the production of polyclonal antibodies, various host animals may be immunized by injection with the antigen such as rabbits, mice, and rats. Various adjuvants may be used to increase the immunological response, depending on the host species, such as Freund's (complete and incomplete), mineral gels (e.g., lysolecithin, pluronic polyols, polyanions, peptides, oil emulsions, keyhole limpet hemocyanin, dinitrophenol), and potentially useful human adjuvants such as BCG (bacille Calmette-Guerin) and *Corynebacterium parvum*.

A monoclonal antibody, which is a substantially homogeneous population of antibodies to a particular antigen, may be obtained by techniques providing for the production of antibody molecules by continuous cell lines in culture. Examples of such techniques include the hybridoma technique described by Kohler and Milstein, *Nature* 256:495–497 (1975) and U.S. Pat. No. 4,376,110, the human B-cell hybridoma technique (Kosbor et al., 1983, *Immunology Today* 4:72; Cole et al., 1983 *Proc. Natl. Acad. Sci. USA* 80:2026–2030), and the EBV-hybridoma technique (Cole et al., 1985, Monoclonal Antibodies And Cancer Therapy, Alan R. Liss, Inc., pp. 77–96).

The hybridoma producing the mAb may be cultivated in vitro or in vivo. Production of high titers of mAbs in vivo makes this the presently preferred method of production.

In addition, techniques developed for the production of "chimeric antibodies" (Morrison et al., 1984, *Proc. Natl. Acad. Sci.*, 81:6851–6855; Neuberger et al., 1984, *Nature*, 312:604–608; Takeda et al., 1985, *Nature*, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, *Science* 242:423–426; Huston et al., 1988, *Proc. Natl. Acad. Sci. USA* 85:5879–5883; and Ward et al., 1989, *Nature* 334:544–546) can be adapted to produce complex-specific single chain antibodies. Single chain antibodies are formed by linking the heavy and light chain fragment of the Fv region via an amino acid bridge, resulting in a single chain polypeptide.

Antibody fragments containing specific binding sites of a complex may be generated by known techniques. For example, such fragments include the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to the receptor tyrosine kinase/adaptor complex.

III. IDENTIFICATION OF APB MODULATING OR BINDING AGENTS

APB binding complexes, proteins containing APB domains and proteins containing APB recognition regions can be used to obtain APB modulating or binding agents Methods for purifying and/or producing such complexes, components of the complexes (i.e., containing a protein having an APB domain and a protein having an APB recognition region) are described herein. Antibodies to such APB binding complexes, proteins containing APB domains and proteins containing APB recognition regions can be obtain as described in section IIC, supra.

APB binding agent may include peptides made of D- and/or L-configuration amino acids (in, for example, the form of random peptide libraries; see Lam, K. S. et al., 1991, *Nature* 354:82–84), phosphopeptides (in, for example, the form of random or partially degenerate, directed phosphopeptide libraries, see Songyang, Z. et al., 1993, Cell 767–778), antibodies, and small organic or inorganic molecules. Synthetic compounds, natural products, and other sources of potentially biologically active materials may be screened in a variety of ways, as described herein. The compounds, antibodies, or other molecules identified may be used as oncogenic disorder treatments.

One method for identifying an agent able to modulate APB mediated activity and/or bind to an APB domain or recognition region involves the following steps:

(a) exposing at least one agent to a protein comprising an APB domain or an APB recognition region for a time sufficient to allow binding of the agent;

(b) removing non-bound agents; and (c) determining the presence of bound agent.

By utilizing this procedure, large numbers of types of molecules may be simultaneously screened for complex component-binding activity.

This approach can be pursued using different techniques. Such as attaching the protein containing the APB domain or recognition region to a solid matrix, such as agarose or plastic beads, microtiter wells, petri dishes, or membranes composed of, for example, nylon or nitrocellulose. The protein can be attached to solid matrix using standard techniques such as by using a component specific antibody bound directly to the solid support.

Molecules exhibiting binding activity may be further screened for an ability to effect APB binding or modulate APB mediated activity. For example, the molecule can be tested for its ability to increase or decrease APB binding. Alternatively, the molecule may be tested for its ability to increase or decrease one or more activities mediated by the APB domain protein.

In another assay, molecules may be directly screened for an ability to promote the APB binding complexes. For example, in vitro complex formation may be assayed by, first, immobilizing a polypeptide containing an APB domain or APB recognition region to a solid support. Second, the immobilized polypeptide is exposed to a potential binding or modulating agent. Third, the ability of the second component (i.e., a polypeptide containing an APB domain or APB recognition region not bound to the support) to form a complex with the immobilized component in the presence of the agent is measured. In addition, one could look for an increase in binding.

Additionally, complex formation in a whole cell may be assayed by utilizing co-immunoprecipitation techniques well known to those of ordinary skill in the art. Briefly, a cell line capable of forming a complex is exposed to a potential modulating or binding agent, and a cell lysate is prepared from this exposed cell line. An antibody raised against one of the components of the complex is added to the cell lysate, and subjected to standard immunoprecipitation techniques. In cases where a complex is still formed the immunoprecipitation will precipitate the complex, whereas in cases where the complex has been disrupted only the complex component to which the antibody is raised will be precipitated.

A preferred method for assessing modulation of complex formation within a cell utilizes a method similar to that described above. Briefly, a cell line capable of forming am APB binding complex is exposed to a test agent. The cells are lysed and the lysate contacted with an antibody specific to one component of the complex, the antibody having been previously bound to a solid support. Unbound material is washed away, and the bound material is exposed to a second antibody binding specifically to a second component of the complex. The amount of second antibody bound is easily detected by techniques well known in the art. Cells exposed to an inhibitory test agent will have formed a lesser amount of complex compared to cells not exposed to the test agent, as measured by the amount of second antibody bound. Cells exposed to a test agent that promotes complex formation will have an increased amount of second antibody bound.

The effect of an agent on the transformation capability of an APB binding complex may be directly assayed. Such agents include those agents identified by utilizing the above screening technique. For example, an agent may be administered to a cell such as a breast cancer cell. The transformation state of the cell may then be measured in vitro, by monitoring, for example, its ability to form colonies in soft agar. Alternatively, a cell's transformation state may be monitored in vivo by, for example, determining its ability to form tumors in immunodeficient nude or severe combined immunodeficiency (SCID) mice.

IV. Purification and Production of Polypeptides

This section describes methods for the synthesis or recombinant expression of polypeptides containing APB domains or APB recognition region. Also described are methods for which cells exhibiting the protein may be expressed.

A. Synthesis and Expression Methods

Methods for the synthesis of polypeptides are well-known to those of ordinary skill in the art. See, for example, Creighton, 1983, Proteins: Structures and Molecular Principles, W. H. Freeman and Co., New York, which is incorporated herein, by reference, in its entirety.

Components of a complex which have been separately synthesized or recombinantly produced, may be reconstituted to form a complex by standard biochemical techniques. For example, samples containing the components of the complex may be combined in a solution buffered with greater than about 150 mM NaCl, at a physiological pH in the range of 7, at room temperature. For example, a buffer comprising 20 mM Tris-HCl, pH 7.4, 137 mM NaCl, 10% glycerol, 1% Triton X-100, 0.1% SDS, 0.5% deoxycholate and 2 mM EDTA could be used.

Polypeptides containing an APB domain or APB recognition region may also be produced using expression vectors encoding the polypeptide. The expression vectors should contain protein coding sequences and appropriate transcriptional/translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., 1989, Molecular Cloning A Laboratory Manual, Cold Spring Harbor Laboratory, New York and Ausubel et al., 1989, Current Protocols in Molecular Biology, Greene Publishing Associates and Wiley Interscience, New York A variety of host-expression vector systems may be utilized to express encoded polypeptides. Such host-expression systems represent vehicles and cells by which the encoded sequence of interest may be produced. Examples include microorganisms such as bacteria (e.g., E. coli, B. subtilis) transformed with recombinant bacteriophage DNA, plasmid DNA or cosmid DNA expression vectors containing protein coding sequences; yeast (e.g., Saccharomyces and Pichia) transformed with recombinant yeast expression vectors containing the protein coding sequences; insect cell systems infected with recombinant virus expression vectors (e.g., baculovirus) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems a number of expression vectors may be advantageously selected depending upon the use intended for the cloned protein. For example, when large quantities of proteins are to be produced for the generation of antibodies or to screen peptide libraries, vectors which direct the expression of high levels of fusion protein products that are readily purified may be desirable. Such vectors include *E. coli* expression vector pUR278 (Ruther et al., 1983, EMBO J. 2:1791), in which the protein coding sequence may be ligated individually into the vector in frame with the lac Z coding region so that a fusion protein is produced; pIN vectors (Inouye & Inouye, 1985, Nucleic acids Res. 13:3101–3109; Van Heeke & Schuster, 1989, J. Biol. Chem. 264:5503–5509).

pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned protein can be released from the GST moiety.

In mammalian host cells, a number of viral based expression systems may be utilized. In cases where an adenovirus is used as an expression vector, the complex coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts. (E.g., See Logan & Shenk, 1984, Proc. Natl. Acad. Sci. U.S.A. 81:3655–3659). Specific initiation signals may also be required for efficient translation of inserted coding sequences. These signals include the ATG initiation codon and adjacent sequences. The efficiency of expression may be enhanced by the inclusion of appropriate transcription enhancer elements, and transcription terminators. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include CHO, VERO, BHK, HeLa, COS, MDCK, 293, 3T3, and WI38.

For long-term, high-yield production of recombinant proteins, stable expression is preferred. For example, cell lines which stably coexpress proteins may be engineered. Rather than using expression vectors which contain viral origins of replication, host cells can be transformed with the protein encoding DNA independently or coordinately controlled by appropriate expression control elements (e.g., promoter, enhancer, sequences, transcription terminators, and polyadenylation sites), and a selectable marker.

Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the APB domain protein and APB recognition protein. Such engineered cell lines are particularly useful in screening and evaluation of agents that affect signals mediated by the complexes.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. U.S.A. 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for dhfr, which confers resistance to methotrexate (Wigler, et al., 1980, Natl. Acad. Sci. U.S.A. 77:3567; O'Hare, et al., 1981, Proc. Natl. Acad. Sci. U.S.A. 78:1527); gpt, which confers resistance to mycophenolic acid (Mulligan & Berg, 1981), Proc. Natl. Acad. Sci. U.S.A. 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

B. Derivatives of Shc APB domain

Also provided herein are functional derivatives of an APB domain present in full length Shc. By "functional derivative" is meant a "chemical derivative," "fragment," "variant," "chimera," or "hybrid" of the APB domain protein. A functional derivative retains at least a portion of the function of the protein, for example reactivity with an antibody specific for the protein, enzymatic activity or binding activity mediated through noncatalytic domains.

A "chemical derivative" contains additional chemical moieties not normally a part of the protein. Covalent modifications of the protein may be introduced by reacting targeted amino acid residues of the peptide with an organic derivatizing agent capable of reacting with selected side chains or terminal residues.

For example, cystienyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and nin-hydrin. Derivatization of arginine residues requires that the reaction be performed in alkaline conditions because of the high $pK_a$ of the guanidine functional group. Furthermore, these reagents may react with the groups of lysine as well as the arginine ε-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the complexes to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[p-azidophenyl)dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195, 128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W. H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, and/or biological half life. The moieties may alternatively eliminate or attenuate an undesirable side effect of a protein agent. Moieties capable of mediating such effects are disclosed, for example, in Remington's Pharmaceutical Sciences, 18th ed., Mack Publishing Co., Easton, Pa. (1990).

The term "fragment" is used to indicate a polypeptide derived from the full length amino acid sequence of a protein. Such a fragment may, for example, be produced by proteolytic cleavage of the full-length protein or using recombinant techniques. Preferably, the fragment is obtained recombinantly by appropriately modifying the DNA sequence encoding the proteins to delete one or more amino acids at one or more sites of the C-terminus, N-terminus, and/or within the native sequence.

Fragments of a protein, when present in a complex resembling the naturally occurring complex, are useful for screening for agents that act to modulate signal transduction. It is understood that such fragments, when present in a complex may retain one or more characterizing portions of the native complex. Examples of such retained characteristics include: substrate specificity, interaction with other molecules in the intact cell, regulatory functions, or binding with an antibody specific for the native complex, or an epitope thereof.

Another functional derivative within the scope of the present invention is a complex comprising at least one "variant" polypeptide which either lack one or more amino acids or contain additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native complex, as described above.

A functional derivative of complexes comprising proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art. The functional derivatives of the complexes typically exhibit the same qualitative biological activity as the native complexes.

V. DIAGNOSIS

The present invention also describes assays which can be used to diagnosis diseases or disorders involving APB mediated activity. Diagnosis can be carried out, for example, by measuring the level of interaction between a protein having an APB domain and a protein having an APB recognition region; measuring the amount of APB domain protein present; and/or measuring the amount of APB recognition region protein present. The measured amounts of these different indicators can be compared to that occurring in healthy individuals and in individuals suffering from a cell proliferative disease or disorder to determine the indicator level associated with the disease or disorder.

Protein complexes involving APB binding may be utilized in a prognostic evaluation of the condition of a patient suspected of exhibiting such a disorder. For example, biological samples obtained from patients suspected of exhibiting a disorder involving a protein complex may be assayed for the presence and amount of such complexes. If such a protein complex is normally present, and the development of the disorder is caused by an abnormal quantity of the complex, the assay should compare complex levels in the biological sample to the range expected in normal tissue of the same cell type.

Alternatively, one or more of the components of the protein complex may be present in an abnormal level or in a modified form, relative to the level or form expected in normal, nononcogenic tissue of the same cell type. It is possible that overexpression of both components of an APB complex may indicate a particularly aggressive disorder.

Thus, an assessment of the individual levels of APB domain protein, APB recognition protein, and mRNA encoding such proteins, in diseased tissue cells may provide valuable clues as to the course of action to be undertaken in treatment. Assays to measure nucleic acid encoding a protein are well known to those of ordinary skill in the art, and may include Northern blot analysis, RNAse protection assays, and PCR for determining mRNA levels. Assays determining protein levels are also well known to those of ordinary skill in the art, and may include Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

VI. ADMINISTRATION

Agents modulating APB activity can be administered to a patient using standard techniques. A particular agent can be administered by itself or in pharmaceutical compositions where it is mixed with suitable carriers or excipient(s). For example, small hydrophobic organic molecules may be directly administered intracellularly.

Toxicity and therapeutic efficacy of APB activity modulating agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents exhibiting large therapeutic indices are preferred.

The data obtained from these cell culture assays and animal studies can be used to formulate a range of dosage for use in human. The dosage of such agents lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays and animal models. For example, a dose can be formulated in animal models to achieve a circulating plasma concentration range that includes the $IC_{50}$ as determined in cell culture (i.e., the concentration of the test agent which achieves a half-maximal modulation of APB mediated activity, measured for example by disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., 1975, in "The Pharmacological Basis of Therapeutics", Ch. 1 p1). A physician of ordinary skill in the art would know how to and when to terminate, interrupt, or adjust administration due to toxicity, or to organ dysfunctions. Conversely, such a physician would also know to adjust treatment to higher levels if the clinical response were not adequate (precluding toxicity).

The magnitude of an administrated dose in the management of the oncogenic disorder of interest will vary with the severity of the condition to be treated. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration, parenteral delivery, including intramuscular, subcutaneous, intramedullary injections, as well as intrathecal, direct intraventricular, intravenous, intraperitoneal, intranasal, and intraocular injections. For injection, the agents of the invention may be formulated in aqueous solutions, preferably in physiologically compatible buffers such as Hanks's solution, Ringer's solution, or physiological saline buffer.

For transmucosal administration, penetrants appropriate to the barrier to be permeated are used in the formulation. Such penetrants are generally known in the art.

With proper choice of carrier and suitable manufacturing practice, the compositions of the present invention, in particular, those formulated as solutions, may be administered parenterally, such as by intravenous injection. The agents can be formulated readily using pharmaceutically acceptable carriers well known in the art into dosages suitable for oral administration. Such carriers enable the agents to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. Molecules present in an aqueous solution at the time of liposome formation may be incorporated into the aqueous interior. The liposomal contents are both protected from the external microenvironment and, because liposomes fuse with cell membranes, are delivered into the cell cytoplasm.

Pharmaceutical compositions suitable for use in the present invention include compositions wherein the active ingredients are contained in an effective amount to achieve its intended purpose. Determination of the effective amounts is well within the capability of those of ordinary skill in the art, especially in light of the detailed disclosure provided herein.

In addition to the active ingredients, these pharmaceutical compositions may contain suitable pharmaceutically acceptable carriers comprising excipients and auxiliaries which facilitate processing of the active agents into preparations which can be used pharmaceutically. Pharmaceutical compositions may be manufactured using techniques such as conventional mixing, dissolving, granulating, dragee-making, levigating, emulsifying, encapsulating, entrapping or lyophilizing processes.

Pharmaceutical formulations for parenteral administration include aqueous solutions of the active agents in water-soluble form. Additionally, suspensions of the active agents may be prepared as appropriate oily injection suspensions. Suitable lipophilic solvents or vehicles include fatty oils such as sesame oil, and synthetic fatty acid esters, such as ethyl oleate or triglycerides, or liposomes. Aqueous injection suspensions may contain substances increasing the viscosity of the suspension, such as sodium carboxymethyl cellulose, sorbitol, or dextran. Optionally, the suspension may also contain suitable stabilizers or agents increasing the solubility of the agents to allow for the preparation of highly concentrated solutions.

The preparations formulated for oral administration may, for example be in the form of tablets, dragees, capsules, or solutions. Pharmaceutical preparations for oral use can be obtained by combining the active agents with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose; and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added.

VII. GENE THERAPY

Gene therapy can be achieved by transferring a gene encoding an APB modulating polypeptide agent into a patient in a manner allowing expression of the polypeptide. Recombinant nucleic acid molecules encoding polypeptide agents can be introduced into a cell in vivo or ex vivo. In vivo transfection techniques include the use of liposomes and retroviral vectors. Miller, *Nature* 357: 455–460, hereby incorporated by reference herein. Ex vivo transfection increases the number of available transfection techniques, but also adds additional complications due to removal and subsequent insertion of cells into a patient.

Nucleotide sequences encoding polypeptide agents which are to be utilized intracellularly may be expressed in the cells of interest, using techniques which are well known to those of ordinary skill in the art. For example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al ., 1989, Molecular Cloning A Laboratory Manual, Cold Spring Harbor Laboratory, New York; Ausubel et al., 1989, Current Protocols in Molecular Biology, Greene Publishing Associates and Wiley Interscience, New York; and Gluzaman, eds. Eukaryotic Viral, Cold Spring Harbor Laboratory, 1982.

VII. EXAMPLES

An example is described below illustrating different aspects and embodiments of the present invention. The example is not intended in any way to limit the disclosed invention.

Shc is a ubiquitously expressed Src homology 2 (SH2) (Src homology 2) domain protein that can transform fibroblasts and differentiate PC12 cells in a RAS-dependent fashion. Shc binds a variety of tyrosine phosphorylated growth factor receptors presumably via its carboxyl-terminal SH2 domain. We cloned a fragment of Shc when screening a bacterial expression library with tyrosine-phosphorylated epidermal growth factor (EGF) (epidermal growth factor) receptor. Surprisingly, this fragment encodes the amino terminus of Shc, a region that has no significant similarity to an SH2 domain. When expressed as a glutathione S-transferase fusion protein, this amino-terminal domain binds to autophosphorylated EGF receptor, as well as HER2/neu and TrkA receptors. This fragment acts like an SH2 domain in that it does not bind non-phosphorylated EGF receptor or EGF receptor with all tyrosine phosphorylation sites mutated or deleted. Our data define a novel domain in Shc that has the potential to interact with growth factor receptors and other tyrosine-phosphorylated proteins.

Growth factor receptors with intrinsic tyrosine kinase activity undergo autophosphorylation on multiple tyrosine residues upon binding ligand. These tyrosine autophosphorylation sites then serve as binding sites for SH2 domain proteins (Fantl, W. J., et al., (1993) *Annu. Rev. Biochem.* 62, 453–481). Genetic and biochemical evidence demonstrates that SH2 domains have a crucial role in the response of cells to growth factors (Pawson, T. and Schlessinger, J. (1993) *Curr. Biol.* 3, 434–442; and Mayer, B. J. and Baltimore, D. (1993) *Trends Cell Biol.* 3, 8–13). Our laboratory has been cloning SH2 domain proteins based on their ability to bind to the tyrosine-phosphorylated EGF receptor (Skolnik, E. Y., et al. (1991) *Cell* 65, 83–90; Lowenstein, E. J., et al. (1992) *Cell* 70, 431–442; and Margolis, B., et al. (1992) *Proc. Natl. Acad. Sci. USA* 89, 8894–8898). This method involves screening bacterial expression libraries with the radioactively labeled carboxyl-terminal tail of the EGF receptor. We have termed the method CORT (Cloning Of Receptor Targets) and the proteins isolated GRBs (Growth Factor Receptor Bound). One of the genes cloned in this manner, Grb2, has homologues in *Caenorhabditis elegans* and *Drosophila melanogaster* and is crucial for viability and development (Schlessinger, J. (1993) *Trends Biochem. Sci.* 18, 273–275). Grb2 binds to a second protein, Son of Sevenless (Sos), which acts as a GDP/GTP exchanger for Ras. In this manner Grb2 acts as an adapter protein coupling growth factor receptor to Ras. Another gene cloned by this method is Grb7, an SH2 domain protein of unknown function that binds to EGF receptor and is overexpressed in breast cancer (Stein, D., et al. (1994) *EMBO J.* 13, 1331–1340).

SH2 domain proteins such as Grb2 and Grb7 bind not only to tyrosine-phosphorylated growth factor receptors but also to tyrosine-phosphorylated cytoplasmic proteins. For example, the SH2 domain protein Shc becomes tyrosine-phosphorylated after EGF receptor activation and binds Grb2 and Grb7 (Stein, D., et al. (1994) *EMBO J.* 13, 1331–1340; Pelicci, G., et al. (1992) *Cell* 70, 93–104; and Rozakis-Adcock, M., et al. (1992) *Nature* 360, 689–692). Shc is expressed as three different proteins of 46, 52 and 66 kDa. The p46$^{Shc}$ and p52$^{Shc}$ forms arise by alternate translational start sites while the p66$^{Shc}$ form is generated by alternate splicing (Pelicci, G., et al. (1992) *Cell* 70, 93–104). Shc tyrosine phosphorylation is induced after cell activation with a variety of growth factors and cytokines (Pelicci, G., et al. (1992) *Cell* 70, 93–104; and Cutler, R. L., et al. (1993) *J. Biol. Chem.* 268, 21463–21465). It is also phosphorylated in cells expressing activated non-receptor tyrosine kinases such as v-src (McGlade, J., et al. (1992) *Proc. Natl. Acad. Sci. USA* 89, 8869–8873). Shc overexpression results in transformation of fibroblasts and differentiation of PC12 cells. The differentiation of PC12 cells is blocked by dominant interfering mutations of Ras consistent with the role of Shc to bind the Grb2-Sos complex (Rozakis-Adcock, M., et al. (1992) *Nature* 360, 689–692).

The interaction of Shc with tyrosine-phosphorylated growth factor receptors such as EGF receptor, TrkA and HER2/neu as well as other tyrosine-phosphorylated proteins such as middle T antigen is well established (Pelicci, G., et al. (1992) *Cell* 70, 93–104; Segatto, O., et al. (1993) *Oncogene* 8, 2105–2112; Obermeier, A., et al. (1994) *EMBO J.* 13, 1585–1590; and Stephens, R. M., et al. (1994) *Nature* 367, 87–90). Shc appears to interact with tyrosine-phosphorylated proteins bearing the sequence, Asn-Pro-X-Tyr (P). This interaction is unusual for SH2 domains that usually select specificity based on amino acids carboxyl-terminal to the phosphotyrosine (Songyang, Z., et al. (1994) *Mol. Cell. Biol.* 14, 2777–2785). Nonetheless, studies have indicated that the specificity of Shc binding to tyrosine-phosphorylated proteins is determined by the SH2 domain (Batzer, A. G., et al. (1994) *Mol. Cell. Biol.* 14, 5192–5201; and Okabayashi, Y., et al. (1994) *J. Biol. Chem.* 269, 18674–18678). In this report we demonstrate that Shc has a second domain in its amino terminus, distinct from the SH2 domain, that can interact with tyrosine-phosphorylated growth factor receptors. The data suggest a novel mechanism whereby signaling molecules can interact with growth factor receptors.

MATERIALS AND METHODS

Library Screening and Cloning of Murine Shc—A randomly primed λEXlox library was prepared from NIH 3T3 cells. Approximately 1 million phages were screened using the tyrosine-phosphorylated carboxyl terminus of the EGF receptor as previously described (Skolnik, E. Y., et al. (1991) *Cell* 65, 83–90; Lowenstein, E. J., et al. (1992) *Cell* 70, 431–442; and Margolis, B., et al. (1992) *Proc. Natl. Acad. Sci. USA* 89, 8894–8898). Nine clones were obtained and will be presented in detail elsewhere. The positive phages were purified, isolated, converted to plasmids, and sequenced as previously described (Margolis, B., et al. (1992) *Proc. Natl. Acad. Sci. USA* 89, 8894–8898). The original insert encoding the first 209 amino acids of p52$^{Shc}$ was then used as a DNA probe to isolate a full-length Shc cDNA from a 16 day embryonic mouse library (Novagen, Madison, Wis.).

DNA Constructs—Using murine p52$^{Shc}$ cDNA as a template, DNA corresponding to the areas of interest were synthesized using polymerase chain reaction with oligonucleotides that contained EcoRI restriction sites to allow for subcloning. The amplified DNA was isolated, digested with EcoRI and subcloned into the pGSTag expression vector (Ron, D. and Dressler, H. (1992) *Biotechniques* 13, 866–869). Deletion mutants were also generated by polymerase chain reaction using standard techniques (Ausubel, F. M., et al. *Current Protocols in Molecular Biology*, (1992) Wiley Interscience, New York). All constructs were sequenced using Sequenase Version 2.0 (U.S. Biochemical Corp.).

Cell Culture—HER 14 cells (NIH 3T3 cells expressing ~4×10$^5$ human EGF receptors/cell), NIH 3T3 cells overexpressing a chimeric receptor that links the extracellular domain of the EGF receptor to the intracellular domain of the HER2/neu (HER 1/2), and NIH 3T3 cells expressing autophosphorylation mutants of the EGF receptor have been described elsewhere (Lee, J., et al. (1989) *EMBO J.* 8, 167–173; Honegger, A. M., et al. (1987) *Cell* 51, 199–209; and Li, N., et al. (1994) *Oncogene* (In Press)). These cells were grown in Dulbecco's modified Eagle's medium with 10% calf serum with 50 U/ml penicillin and 50 µg/ml streptomycin. PC12 cells were grown in Dulbecco's modified Eagle's medium with 10% horse serum, 5% fetal calf serum, and penicillin/streptomycin. NIH 3T3 cells were starved overnight in 1% calf serum and then stimulated with EGF for 3 min. PC12 cells were starved for 48 hours in 1 fetal calf serum and 1% horse serum and then stimulated with nerve growth factor for five min. Cells were lysed in 1% Triton X-100 lysis buffer containing protease and phosphatase inhibitors (Margolis, B., et al. (1989) *Cell* 57, 1101–1107).

Antibodies—To analyze EGF receptor, mAb (monoclonal antibody) 108 was used for immunoprecipitation while antipeptide antibodies, anti-C and anti-F, were used for immunoblotting as previously described (Margolis, B., et al. (1990) *EMBO J.* 9, 4375–4380). Rabbit polyclonal TrkA antibodies were purchased from Oncogene Science (Uniondale, N.Y). Polyclonal GST (glutathione S-transferase) antibodies were prepared by injecting rabbits with purified GST protein and anti-phosphotyrosine antibodies were prepared as previously described (Margolis, B., et al. (1990) *EMBO J.* 9, 4375–4380).

Binding Studies—GST fusion proteins were expressed using standard techniques (Ausubel, F. M., et al. *Current Protocols in Molecular Biology*, (1992) Wiley Interscience, New York). Protein concentration was determined by SDS-PAGE (polyacrylamide gel electrophoresis) using bovine serum albumin as a standard. Lysates were incubated with GST fusion proteins bound to glutathione-agarose beads for 90 minutes at 4° C. The beads were then washed three times with HNTG (20 mM Hepes, pH 7.5, 150 mM NaCl, 10% glycerol, and 0.1% Triton X-100), boiled in 1× sample buffer, and separated by SDS-PAGE. Transfer and immunoblotting were performed as described (Margolis, B., et al. (1989) *Cell* 57, 1101–1107). In other studies, EGF receptor was immunoprecipitated with mAb 108 and washed three times with HNTG. Receptors were then phosphorylated in vitro using 5 mM MnCl$_2$ and 50 µM ATP in HNTG. After washing three more times with HNTG, 1 ml of 1% Triton X-100 lysis buffer containing 5 µg of GST fusion protein as well as protease and phosphatase inhibitors was added to the immobilized receptors. After incubating for 90 minutes at 4° C., samples were washed three more times with HNTG and boiled in 1x sample buffer. Forty microliters of post binding supernatant and the bound proteins were separated by SDS-PAGE, transferred to nitrocellulose, and blotted with anti-GST.

RESULTS AND DISCUSSION

In an effort to isolate new Grb proteins we generated a randomly primed bacterial expression library from NIH 3T3 cells. One clone, Grb12, bound to the probe with a similar as that seas that seen with other clones isolated in this screen such as one encoding the SH2 domain of Grb2 (FIG. 1A). Surprisingly, Grb12 did not contain an SH2 domain but rather encoded 209 amino acids of murine Shc identical to the amino terminus of human $p52^{Shc}$. We proceeded to clone the cDNA that encoded the full-length murine $p52^{Shc}$ and found it to be 96% identical to human Shc (FIG. 1B).

Figure 2B:
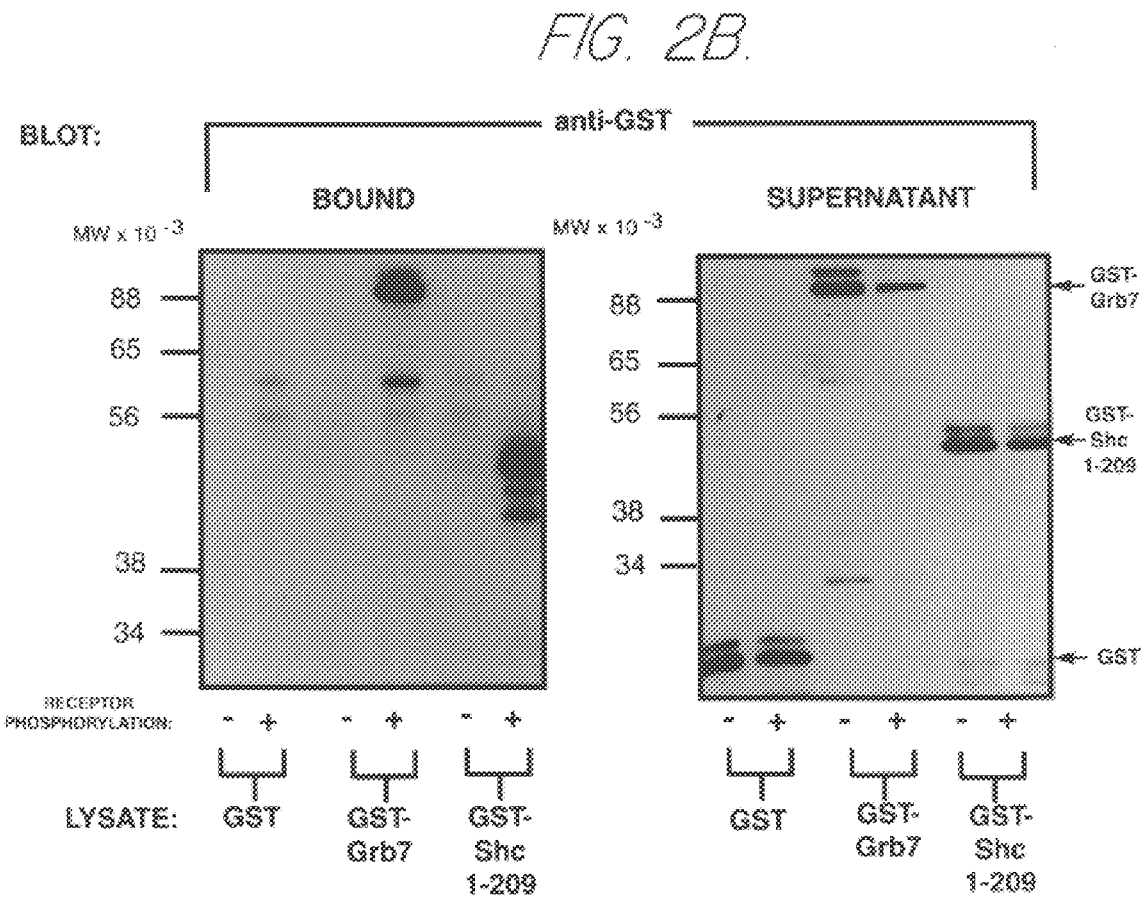
Figure 3:
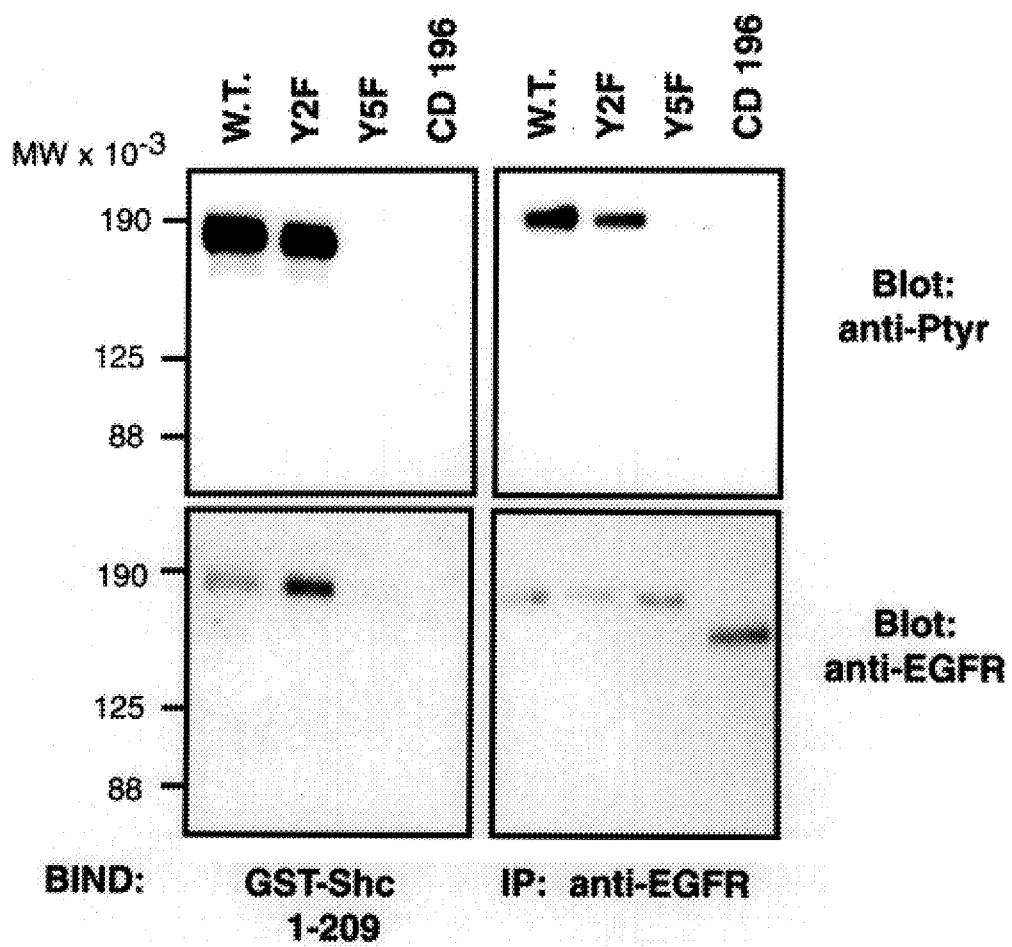
FIG. 3. Association of GST-Shc 1-209 with mutant forms of the EGF receptor. NIH 3T3 cells overexpressing various EGF receptor mutants were stimulated with EGF (200 ng/ml) for 3 min and then lysed. Wild type EGF receptor (W.T.) contains all five known EGF receptor autophosphorylation sites, Y2F has Tyr-992 and Tyr-1068 mutated to phenylalanine, Y5F has all five known EGF receptor autophosphorylation sites mutated to phenylalanine, and CD196 has a carboxyterminal deletion of 196 amino acids deleting all known autophosphorylation sites (Li, N., et al. (1994) *Oncogene* (In Press). Beads containing GST-Shc 1-209 fusion protein (3 μg) were added to the various lysates containing equal amounts of the receptor (left panels) or the lysates were immunoprecipitated with the anti-EGF receptor (EGFR) antibody (mAb108) (right panels). All samples were incubated at 4° C. for 90 min. The bound proteins were then washed, subjected to SDS-PAGE and transferred to nitrocellulose. The membranes were immunoblotted with anti-phosphotyrosine (anti-Ptyr) antibody (upper panels) and anti-EGFR (anti-F; lower panels). IP, immunoprecipitate.

These results were interesting because they suggested that Shc might interact with growth factor receptors in a novel fashion. Accordingly we examined the binding of the Shc amino terminus (hereafter referred to as Shc 1-209) in further detail. First we determined if the binding of Shc 1-209 was dependent on EGF receptor activation. To perform these studies we generated Shc 1-209 as a GST fusion protein and examined its ability to bind EGF receptor from lysates of NIH 3T3 cells. We found that, like the Grb7 SH2 domains, Shc 1-209 bound only to the activated tyrosine-phosphorylated receptor and not to the inactive non-phosphorylated receptor (FIG. 2A). We asked if this binding was dependent on receptor autophosphorylation. EGF receptor was immunoprecipitated from unstimulated cells and then tyrosine-phosphorylated in vitro by adding $Mn^{2+}$ and ATP. We then added bacterial lysates expressing Shc 1-209 and found that Shc 1-209 bound directly to phosphorylated but not non-phosphorylated receptors (FIG. 2B). To confirm that the binding was dependent on autophosphorylation, we examined the binding of Shc 1-209 to EGF receptor mutants lacking autophosphorylation sites. We found that mutation of all EGF receptor tyrosine-phosphorylated residues to phenylalanine or deletion of the EGF receptor carboxyl terminus completely eliminated Shc 1-209 binding (FIG. 3). It was found that while 30 mM phosphotyrosine could partially inhibit the binding of Shc 1-209 to the EGF receptor, it completely inhibited the binding of the Grb7 SH2 domain to this receptor (results not shown). This may represent a difference in the affinity of interactions or a basic difference in the molecular mechanism of EGF receptor interaction with Shc 1-209 versus SH2 domains.

Figure 4A:
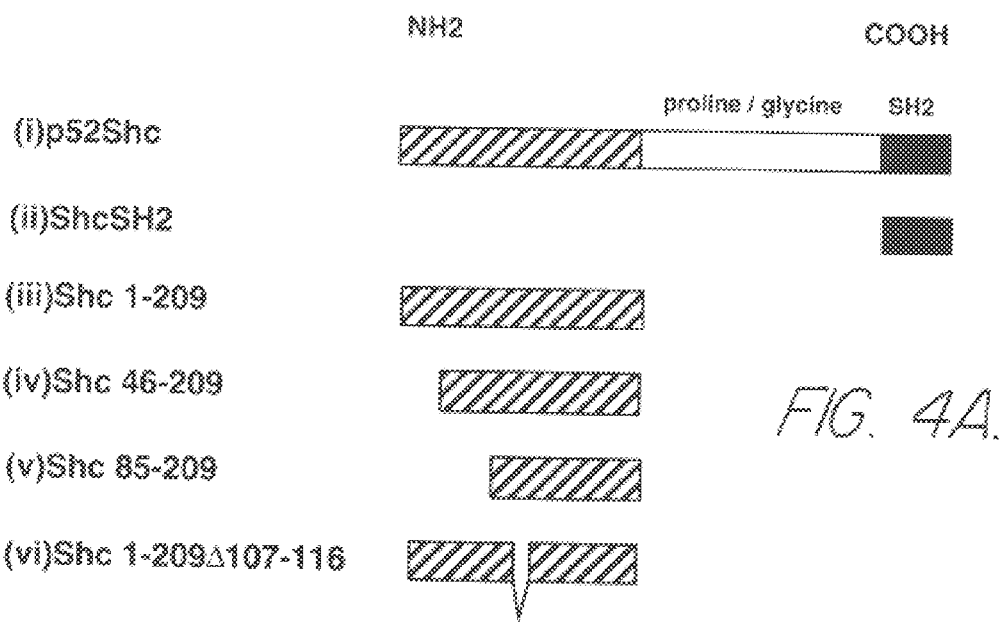
FIGS. 4A, 4B, 4C and 4D. Binding of Shc fragments to growth factor receptors.
Figure 4B:
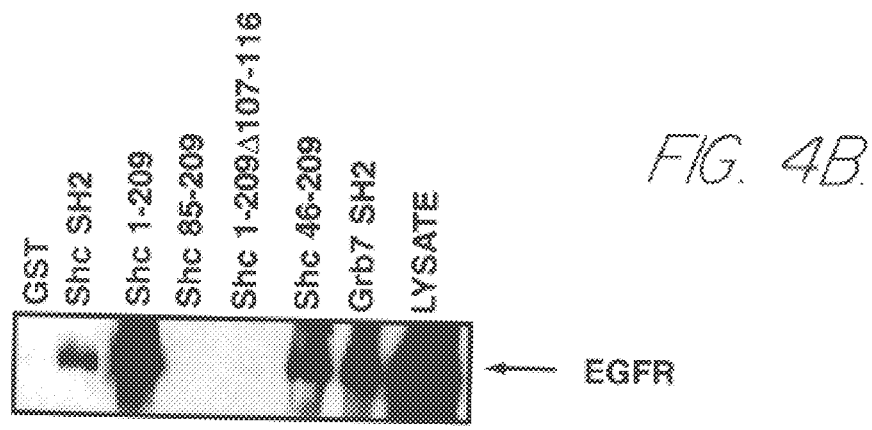

The binding of Shc 1-209 was compared to the binding of the Shc SH2 domain to EGF receptor. Consistently, we found that the EGF receptor binding of Shc 1-209 was comparable or superior to that observed with the Shc SH2 domain (FIG. 4B). This was found not only with the murine Shc SH2 domain, but also with the human Shc SH2 domain (results not shown). Furthermore we found that Shc 1-209 bound to HER2/neu and TrkA (FIGS. 4, C and D). In the case of TrkA, Shc 1-209 appeared to bind in a similar fashion to that seen with the SH2 domain of phospholipase C-λ.

Figure 4C:
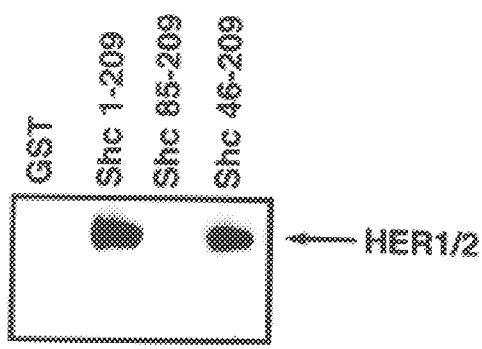
Figure 4D:
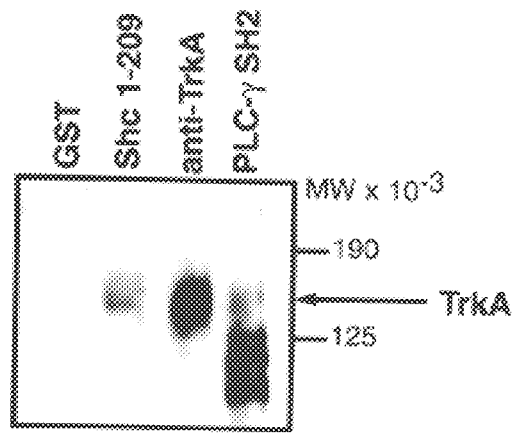

$p46^{Shc}$ is encoded by a protein that begins 46 amino acids carboxyl-terminal to the start site for p52. We asked if the amino acids encoding the amino terminus of $p46^{Shc}$, i.e. Shc 46–209, could also bind to growth factor receptors. Our results indicate that this domain as present in $p46^{Shc}$ can bind both EGF receptor and HER2/neu receptor. However a construct with a more severe amino-terminal deletion, Shc 85–209, did not bind growth factor receptors nor did a construct Shc 1-209Δ106-117 with amino acids 106–117 deleted (FIGS. 4A–C).

In summary, our results reveal a novel growth factor receptor binding domain in the amino terminus of Shc. The binding to the EGF receptor appears direct and tyrosine phosphorylation dependent in a fashion similar to that seen with the SH2 domain. Although the domain behaves like an SH2 domain, sequence analysis of this domain reveals no significant similarity to SH2 domain proteins or any other protein in the data base. The binding is not dependent on fusion of this domain to GST as binding was also seen in the library screening where Shc 1-209 was fused to gene 10 of the T7 phage. This result appears to reveal a new mechanism whereby proteins can interact with growth factor receptors and other tyrosine-phosphorylated proteins.

One however must approach the data presented here with some caution. All our studies are based on in vitro interactions with fusion proteins that may not be representative of what is seen with the full-length Shc protein. We have just begun to study the effect of SH2 domain and amino-terminal domain mutations on the binding of full-length Shc expressed in mammalian cells. Mutations in the highly conserved FLVR sequence in the SH2 domain appear to reduce the binding of Shc to EGF receptor by approximately 90%. In contrast, deletions in the amino-terminal domain (such as the removal of the amino-terminal 85 amino acids) reduce the binding of Shc to EGF receptor by only 50%. Thus these preliminary observations suggest the amino-terminal domain can cooperate with the SH2 domain to promote binding to growth factor receptors. This might be akin to the cooperative effect seen when the two SH2 domains of phosphatidylinositol 3 kinase associated p85 bind to the platelet-derived growth factor receptor (Kashishian, A., et al. (1992) EMBO J. 11, 1373–1382). It might also explain the high stoichiometry of association between Shc and EGF receptor (Soler, C., et al. (1994) J. Biol. Chem. 269, 12320–12324). It is not entirely clear why the amino terminus cannot completely compensate for reductions in the SH2 domain binding when one considers the strength of binding we have observed with GST fusion proteins or in the library screening. Without knowledge of the structure of the Shc protein it is difficult to know whether the amino terminus of Shc is always surface exposed and able to play a role in protein-protein interactions. The binding of the amino-terminal domain to proteins may also be affected by reversible modification such as phosphorylation. It is also possible that the amino-terminal domain may play an important role in binding only a specific subset of tyrosine-phosphorylated proteins.

The role of the amino-terminal domain in the physiologic interaction of Shc with tyrosine-phosphorylated proteins is unknown. Yet the observation that the amino terminus of Shc when expressed alone binds tightly to several different growth factor receptors is striking. It is possible that the amino terminus of Shc might in some fashion contribute to the unusual ability of Shc to bind the Asn-Pro-X-Tyr (P) motif. It is clear that there is much more to learn about the molecular basis of Shc function and its interaction with growth factor receptors. Our findings indicate that there may be a heretofore unappreciated mechanism whereby signaling molecules can interact in a specific fashion with tyrosine-phosphorylated proteins. Further studies on the function of the Shc amino-terminal domain should provide insight into this problem.

Other embodiments are within the following claims.

What is claimed is:

1. A purified polypeptide comprising an amino acid sequence which is identical to amino acids 46–209 of p52$^{shc}$ as set forth in SEQ ID NO:2, wherein said polypeptide is not full length Shc.

2. The polypeptide of claim 1, wherein said polypeptide has been substantially purified to provide at least 85% of the total protein present in a preparation.

3. The polypeptide of claim 1, wherein said polypeptide binds to a receptor tyrosine kinase which is phosphorylated, but does not bind to said receptor tyrosine kinase when the latter is not phosphorylated and has been substantially purified to provide at least 85% of the total protein present in a preparation.

4. The polypeptide of claim 1, wherein said polypeptide binds to phosphorylated epidermal growth factor receptor, but does not bind to unphosphorylated epidermal growth factor receptor and has been substantially purified to provide at least 85% of the total protein present in a preparation.

5. A purified polypeptide comprising an amino acid sequence region of at least 80% sequence similarity or at least 75% sequence identity to amino acids 46–209 of p52$^{shc}$ as set forth in SEQ ID NO:2, wherein said polypeptide is not full length Shc and said polypeptide binds to an APB recognition domain present in a protein tyrosine kinase.

6. The polypeptide of claim 5, wherein said polypeptide consists of said amino acid sequence region and said polypeptide has been substantially purified to provide at least 85% of the total protein present in a preparation.

7. The polypeptide of claim 5, wherein said polypeptide binds to a receptor tyrosine kinase which is phosphorylated but does not bind to said receptor tyrosine kinase when the latter is not phosphorylated and has been substantially purified to provide at least 85% of the total protein present in a preparation.

8. The polypeptide of claim 5, wherein said polypeptide binds to phosphorylated epidermal growth factor receptor but does not bind to unphosphorylated epidermal growth factor receptor; and has been substantially purified to provide at least 85% of the total protein present in a preparation.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 469 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Met Asn Lys Leu Ser Gly Gly Gly Gly Arg Arg Thr Arg Val Glu Gly
 1               5                  10                  15
Gly Gln Leu Gly Gly Glu Glu Trp Thr Arg His Gly Ser Phe Val Asn
                20                  25                  30
Lys Pro Thr Arg Gly Trp Leu His Pro Asn Asp Lys Val Met Gly Pro
                35                  40                  45
Gly Val Ser Tyr Leu Val Arg Tyr Met Gly Cys Val Glu Val Leu Gln
            50                  55                  60
Ser Met Arg Ala Leu Asp Phe Asn Thr Arg Thr Gln Val Thr Arg Glu
65                  70                  75                  80
Ala Ile Ser Leu Val Cys Glu Ala Val Pro Gly Ala Lys Gly Ala Thr
                85                  90                  95
Arg Arg Arg Lys Pro Cys Ser Arg Pro Leu Ser Ser Ile Leu Gly Arg
                100                 105                 110
Ser Asn Leu Lys Phe Ala Gly Met Pro Ile Thr Leu Thr Val Ser Thr
                115                 120                 125
Ser Ser Leu Asn Leu Met Ala Ala Asp Cys Lys Gln Ile Ile Ala Asn
            130                 135                 140
His His Met Gln Ser Ile Ser Phe Ala Ser Gly Gly Asp Pro Asp Thr
145                 150                 155                 160
Ala Glu Tyr Val Ala Tyr Val Ala Lys Asp Pro Val Asn Gln Arg Ala
                165                 170                 175
Cys His Ile Leu Glu Cys Pro Glu Gly Leu Ala Gln Asp Val Ile Ser
                180                 185                 190
Thr Ile Gly Gln Ala Phe Glu Leu Arg Phe Lys Gln Tyr Leu Arg Asn
            195                 200                 205
Pro Pro Lys Leu Val Thr Pro His Asp Arg Met Ala Gly Phe Asp Gly
    210                 215                 220
Ser Ala Trp Asp Glu Glu Glu Glu Pro Pro Asp His Gln Tyr Tyr
225                 230                 235                 240
Asn Asp Phe Pro Gly Lys Glu Pro Pro Leu Gly Gly Val Val Asp Met
                245                 250                 255
Arg Leu Arg Glu Gly Ala Ala Arg Pro Thr Leu Pro Ser Ala Gln Met
                260                 265                 270
Ser Ser His Leu Gly Ala Thr Leu Pro Ile Gly Gln His Ala Ala Gly
                275                 280                 285
Asp His Glu Val Arg Lys Gln Met Leu Pro Pro Pro Cys Pro Gly
            290                 295                 300
Arg Glu Leu Phe Asp Asp Pro Ser Tyr Val Asn Ile Gln Asn Leu Asp
305                 310                 315                 320
```

```
Lys  Ala  Arg  Gln  Ala  Gly  Gly  Gly  Ala  Gly  Pro  Pro  Asn  Pro  Ser  Leu
               325                      330                     335

Asn  Gly  Ser  Ala  Pro  Arg  Asp  Leu  Phe  Asp  Met  Lys  Pro  Phe  Glu  Asp
               340                      345                     350

Ala  Leu  Arg  Val  Pro  Pro  Pro  Gln  Ser  Met  Ser  Ala  Glu  Gln
          355                      360                     365

Leu  Gln  Gly  Glu  Pro  Trp  Phe  His  Gly  Lys  Leu  Ser  Arg  Arg  Glu  Ala
          370                      375                     380

Glu  Ala  Leu  Leu  Gln  Leu  Asn  Gly  Asp  Phe  Leu  Val  Arg  Glu  Ser  Thr
385                      390                      395                          400

Thr  Thr  Pro  Gly  Gln  Tyr  Val  Leu  Thr  Gly  Leu  Gln  Ser  Gly  Gln  Pro
                    405                      410                     415

Lys  His  Leu  Leu  Leu  Val  Asp  Pro  Glu  Gly  Val  Val  Arg  Thr  Lys  Asp
               420                      425                     430

His  Arg  Phe  Glu  Ser  Val  Ser  His  Leu  Ile  Ser  Tyr  His  Met  Asp  Asn
          435                      440                     445

His  Leu  Pro  Ile  Ile  Ser  Ala  Gly  Ser  Glu  Leu  Cys  Leu  Gln  Gln  Pro
     450                      455                     460

Val  Asp  Arg  Lys  Val
465
```

( 2 ) INFORMATION FOR SEQ ID NO:2:

( i ) SEQUENCE CHARACTERISTICS:
        ( A ) LENGTH: 473 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Asn  Lys  Leu  Ser  Gly  Gly  Gly  Arg  Arg  Thr  Arg  Val  Glu  Gly
1                   5                        10                      15

Gly  Gln  Leu  Gly  Gly  Glu  Glu  Trp  Thr  Arg  His  Gly  Ser  Phe  Val  Asn
               20                       25                      30

Lys  Pro  Thr  Arg  Gly  Trp  Leu  His  Pro  Asn  Asp  Lys  Val  Met  Gly  Pro
               35                       40                      45

Gly  Val  Ser  Tyr  Leu  Val  Arg  Tyr  Met  Gly  Cys  Val  Glu  Val  Leu  Gln
     50                       55                       60

Ser  Met  Arg  Ala  Leu  Asp  Phe  Asn  Thr  Arg  Thr  Gln  Val  Thr  Arg  Glu
65                       70                       75                           80

Ala  Ile  Ser  Leu  Val  Cys  Glu  Ala  Val  Pro  Gly  Ala  Lys  Gly  Ala  Thr
                    85                       90                      95

Arg  Arg  Arg  Lys  Pro  Cys  Ser  Arg  Pro  Leu  Ser  Ser  Ile  Leu  Gly  Arg
               100                      105                     110

Ser  Asn  Leu  Lys  Phe  Ala  Gly  Met  Pro  Ile  Thr  Leu  Thr  Val  Ser  Thr
          115                      120                      125

Ser  Ser  Leu  Asn  Leu  Met  Ala  Ala  Asp  Cys  Lys  Gln  Ile  Ile  Ala  Asn
     130                      135                      140

His  His  Met  Gln  Ser  Ile  Ser  Phe  Ala  Ser  Gly  Gly  Asp  Pro  Asp  Thr
145                      150                      155                         160

Ala  Glu  Tyr  Val  Ala  Tyr  Val  Ala  Lys  Asp  Pro  Val  Asn  Gln  Arg  Ala
               165                      170                     175

Cys  His  Ile  Leu  Glu  Cys  Pro  Glu  Gly  Leu  Ala  Gln  Asp  Val  Ile  Ser
               180                      185                     190

Thr  Ile  Gly  Gln  Ala  Phe  Glu  Leu  Arg  Phe  Lys  Gln  Tyr  Leu  Arg  Asn
```

-continued

```
            195                           200                           205
Pro  Pro  Lys  Leu  Val  Thr  Pro  His  Asp  Arg  Met  Ala  Gly  Phe  Asp  Gly
     210                      215                 220

Ser  Ala  Trp  Asp  Glu  Glu  Glu  Glu  Pro  Pro  Asp  His  Gln  Tyr  Tyr
225                      230                 235                           240

Asn  Asp  Phe  Pro  Gly  Lys  Glu  Pro  Pro  Leu  Gly  Gly  Val  Val  Asp  Met
                    245                      250                      255

Arg  Leu  Arg  Glu  Gly  Ala  Ala  Pro  Gly  Ala  Ala  Arg  Pro  Thr  Ala  Pro
               260                      265                 270

Asn  Ala  Gln  Thr  Pro  Ser  His  Leu  Gly  Ala  Thr  Leu  Pro  Val  Gly  Gln
          275                      280                      285

Pro  Val  Gly  Gly  Asp  Pro  Glu  Val  Arg  Lys  Gln  Met  Pro  Pro  Pro  Pro
     290                      295                 300

Pro  Cys  Pro  Gly  Arg  Glu  Leu  Phe  Asp  Asp  Pro  Ser  Tyr  Val  Asn  Val
305                      310                 315                           320

Gln  Asn  Leu  Asp  Lys  Ala  Arg  Gln  Ala  Val  Gly  Gly  Ala  Gly  Pro  Pro
               325                      330                      335

Asn  Pro  Ala  Ile  Asn  Gly  Ser  Ala  Pro  Arg  Asp  Leu  Phe  Asp  Met  Lys
               340                      345                 350

Pro  Phe  Glu  Asp  Ala  Leu  Arg  Val  Pro  Pro  Pro  Gln  Ser  Val  Ser
          355                      360                 365

Met  Ala  Glu  Gln  Leu  Arg  Gly  Glu  Pro  Trp  Phe  His  Gly  Lys  Leu  Ser
     370                      375                 380

Arg  Arg  Glu  Ala  Glu  Ala  Leu  Leu  Gln  Leu  Asn  Gly  Asp  Phe  Leu  Val
385                      390                 395                           400

Arg  Glu  Ser  Thr  Thr  Thr  Pro  Gly  Gln  Tyr  Val  Leu  Thr  Gly  Leu  Gln
               405                      410                      415

Ser  Gly  Gln  Pro  Lys  His  Leu  Leu  Leu  Val  Asp  Pro  Glu  Gly  Val  Val
               420                      425                 430

Arg  Thr  Lys  Asp  His  Arg  Phe  Glu  Ser  Val  Ser  His  Leu  Ile  Ser  Tyr
          435                      440                 445

His  Met  Asp  Asn  His  Leu  Pro  Ile  Ile  Ser  Ala  Gly  Ser  Glu  Leu  Cys
     450                      455                 460

Leu  Gln  Gln  Pro  Val  Glu  Arg  Lys  Leu
465                      470
```